(12) United States Patent
Hegde et al.

(10) Patent No.: US 11,547,777 B2
(45) Date of Patent: Jan. 10, 2023

(54) THERMALLY ROBUST, ELECTROMAGNETIC INTERFERENCE COMPATIBLE, DEVICES FOR NON-INVASIVE AND INVASIVE SURGERY

(71) Applicant: The Regents of the University of California, Oakland, CA (US)

(72) Inventors: Sanjeet Hegde, San Diego, CA (US); Kanishka Ratnayaka, San Diego, CA (US); John Moore, San Diego, CA (US); Sunghoon Park, Seoul (KR); Prabhakar Bandaru, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 172 days.

(21) Appl. No.: 16/626,811

(22) PCT Filed: Jun. 26, 2018

(86) PCT No.: PCT/US2018/039514
§ 371 (c)(1),
(2) Date: Dec. 26, 2019

(87) PCT Pub. No.: WO2019/005802
PCT Pub. Date: Jan. 3, 2019

(65) Prior Publication Data
US 2020/0114042 A1     Apr. 16, 2020

Related U.S. Application Data

(60) Provisional application No. 62/525,034, filed on Jun. 26, 2017.

(51) Int. Cl.
*A61L 27/30* (2006.01)
*B82Y 30/00* (2011.01)
(Continued)

(52) U.S. Cl.
CPC ........... *A61L 27/306* (2013.01); *A61L 29/103* (2013.01); *A61L 29/106* (2013.01); *A61L 31/088* (2013.01);
(Continued)

(58) Field of Classification Search
CPC ...................................... B82Y 30/00
See application file for complete search history.

(56) References Cited

U.S. PATENT DOCUMENTS

| 7,662,467 B2 * | 2/2010 | Li | ............................ C08L 63/00 428/298.4 |
| 2002/0002246 A1 * | 1/2002 | Wang | ...................... C08L 23/00 525/240 |

(Continued)

OTHER PUBLICATIONS

Clogenson et al. Catheters and guidewires for interventional MRI: are we there yet. Imaging Med. 8(2) pp. 39-43 (2016) (Year: 2016).*

(Continued)

*Primary Examiner* — Cachet I Proctor
(74) *Attorney, Agent, or Firm* — Perkins Coie LLP

(57) ABSTRACT

Techniques to fabricate and use a nanocomposite coating that includes one or more nanotubes such as carbon nanotubes are disclosed. In some examples, a guidewire may include the nanocomposite material. The guidewire is immune to electromagnetic interference, is thermally robust, and is capable of accommodating inactive markers and active electronics.

16 Claims, 14 Drawing Sheets

(51) Int. Cl.
  *A61L 29/10* (2006.01)
  *A61L 31/08* (2006.01)
(52) U.S. Cl.
  CPC ........... *B82Y 30/00* (2013.01); *A61L 2400/12* (2013.01); *A61L 2420/06* (2013.01)

(56) References Cited

U.S. PATENT DOCUMENTS

| | | | |
|---|---|---|---|
| 2006/0100696 A1* | 5/2006 | Atanasoska | A61L 31/18 623/1.44 |
| 2006/0121080 A1* | 6/2006 | Lye | A61L 31/18 623/1.42 |
| 2007/0067882 A1* | 3/2007 | Atanasoska | A61L 29/085 606/192 |
| 2007/0282247 A1* | 12/2007 | Desai | A61L 29/16 604/19 |
| 2008/0160856 A1* | 7/2008 | Chen | A61F 13/537 442/341 |
| 2009/0068244 A1* | 3/2009 | Weber | A61L 27/443 424/423 |
| 2010/0068461 A1* | 3/2010 | Wallace | B81C 1/00111 428/156 |
| 2010/0136327 A1 | 6/2010 | Ma et al. | |
| 2011/0046461 A1 | 2/2011 | McKenna | |
| 2011/0263966 A1* | 10/2011 | Geistert | A61N 1/05 600/411 |
| 2013/0108826 A1* | 5/2013 | Chakravarthi | H01B 13/0036 428/114 |

OTHER PUBLICATIONS

Abernethy, R. The New Weibull Handbook Robert B. Abernethy, North Palm Beach, FL, 2003.
Antoniotti, S. et al. "Acid-catalysed oxidative ring-opening of epoxide by DMSO. Theoretical investigation of the effect of acid catalysts and substituents" Theor. Chem Acc 112, 290-297 (2004).
Balberg, I. et al. "Excluded volume and its relation to the onset of percolation" Phys. Rev. B., vol. 30, No. 7, 3933-3943. (1984).
Balberg, I. "Universal percolation-threshold limits in the continuum" Phys. Rev. B, vol. 31, No. 6, 4053-4055. (1985).
Bandaru, P.R. "Electrical properties and applications of carbon nanotube structures" J. Nanosci. Nanotechnol. 7, 1239-1267 (2007).
Berber, S. et al., "Unusually High Thermal Conductivity of Carbon Nanotubes" Phys. Rev. Lett., vol. 84, No. 20, 4613-4616. (2002).
Biercuk, M.J., et al., "Carbon nanotube composites for thermal management" Appl. Phys. Lett., vol. 80, 2767-2769. (2002).
Bigg, D. M. et al., "Plastic Composites for Electromagnetic Interference Shielding Applications" Polym. Compos.,, vol. 4, No. 1, 40-46. (1983).
Bonnet, P. et al., "Thermal properties and percolation in carbon nanotube-polymer composites" Appl. Phys. Lett., vol. 91, 201910, 4 pages. (2007).
Borca-Tasciuc, T., et al., "Data reduction in 3ω method for thin-film thermal conductivity determination" Rev. Sci. Instrum., vol. 72, 2139-2147. (2001).
Cahill, D.G. "Thermal conductivity measurement from 30 to 750 K: the 3ω method" Rev. Sci. Instrum., vol. 61, 802-808. (2008).
Carslaw, H.S., et al., Conduction of Heat in Solids, 2 ed. (Oxford University Press, New York, 1986).
Celzard, A., et al., "Critical concentration in percolating systems containing a high-aspect-ratio filler" Phys. Rev. B vol. 53, 6209-6214 (1996).
Chung, D.D.L., "Electromagnetic interference shielding effectiveness of carbon materials" Carbon vol. 39, 279-285 (2001).
Ci, L. et al., "Continuous Carbon Nanotube Reinforced Composites" Nano Lett. 8, 2762-2766 (2008).
Clogenson, H. et al. "Catheters and Guidewires for Interventional MRI: Are We There Yet?" Journal of Imaging and Interventional Radiology, vol. 8, No. 2, 39-43 (2016).
Du, F. et al., "Effect of nanotube alignment on percolation conductivity in carbon nanotube/polymer composites" Phys. Rev. B vol. 72, 121404(R) 4 pages (2005).
Fasoli et al. "Self-assembled nanotube field-effect transistors for label-free protein biosensors" Journal of Applied Physics 104, 074310, 6 pages (2008).
Foygel, M. et al., "Theoretical and computational studies of carbon nanotube composites and suspensions: Electrical and thermal conductivity" Phys. Rev. B, 71, 104201, 8 pages (2005).
Hughes, M. Dekker Encyclopedia of Nanoscience and Nanotechnology (Taylor & Francis, London, 2004), pp. 447-459.
Huxtable, S.T., et al., "Interfacial heat flow in carbon nanotube suspensions" Nature Mater. 2, 731-734 (2003).
ISA, International Search Report and Written Opinion for International Application No. PCT/US2018/039514, dated Aug. 31, 2018. 9 pages.
Ishida, M. et al. "Estimating the yield and characteristics of random network carbon nanotube transistors" Appl. Phys. Lett. 92, 163507, 4 pages (2008).
Kang, S.J. et al. "High-performance electronics using dense, perfectly aligned arrays of single-walled carbon nanotubes" Nature Nanotech 2, 230-236 (2007).
Kirkpatrick, S. "Percolation and Conduction" Rev. Mod. Phys. 45, 574-588 (1973).
Kumar S. et al. "Theory of transfer characteristics of nanotube network transistors" Appl. Phys. Lett. 88, 123505 (2006).
Landauer, R., "Electrical conductivity in inhomogeneous media" AIP Conf. Proc. 40, 2-45 (1978).
Li, N. et al. "Electromagnetic Interference (EMI) Shielding of Single-Walled Carbon Nanotube Epoxy Composites" Nano Lett. 2006, 6, 6, 1141-1145.
Nichols, J. et al. "Artificial introduction of defects into vertically aligned multiwalled carbon nanotube ensembles: Application to electrochemical sensors" Journal of Applied Physics 102, 064306 (2007).
Onsager, L. "The Effects of Shape on the Interaction of Colloidal Particles" Annals of the New York Academy of Sciences, vol. 51, Issue 4. 627. (1949).
Park, S-H. et al. "Enhanced dielectric constants and shielding effectiveness of, uniformly dispersed, functionalized carbon nanotube composites" Appl. Phys. Lett. 94, vol. 243111, 4 pages (2009).
Park, S-H. et al. "Modeling the electrical resistivity of polymer composites with segregated structures" IEEE Trans. Nanotechnol. 9, 464-469 (2010).
Pfeifer, S. et al., "A methodology for quantitatively characterizing the dispersion of nanostructures in polymers and composites," Materials Research Letters, vol. 2, No. 3, 166-175 (2014).
Pfeifer, S. et al., "Analysis of electrical percolation thresholds in carbon nanotube networks using the Weibull probability distribution" J. Appl. Phys. 108, 024305 (2010).
Shenogina, N., et al., "On the lack of thermal percolation in carbon nanotube composites" Appl. Phys. Lett. 87, 133106. 4 pages (2005).
Shklovskii, B.I., et al., Electronic Properties of Doped Semiconductors (Springer-Verlag, New York, NY, 1984).
Stauffer, D. et al., Introduction to Percolation Theory (CRC Press, Boca Raton, FL, 1994).
Straley, J.P., "Critical exponents for the conductivity of random resistor lattices" Phys. Rev. B vol. 15, No. 12, 5733-5737 (1977).
White, S.L., et al., "Simulations and electrical conductivity of percolated networks of finite rods with various degrees of axial alignment" Phys. Rev. B 79, 024301,6 pages (2009).
Yu, M-F. et al. "Strength and Breaking Mechanism of Multiwalled Carbon Nanotubes Under Tensile Load" Science; vol. 287, Issue 5453, pp. 637-640 (2000).

* cited by examiner

THERMALLY ROBUST, ELECTROMAGNETIC INTERFERENCE COMPATIBLE, DEVICES FOR NON-INVASIVE AND INVASIVE SURGERY

CROSS REFERENCE TO RELATED APPLICATIONS

This patent document is a 371 National Phase Application of International Application No. PCT/US2018/039514, filed on Jun. 26, 2018, which claims the benefit of priority of U.S. Provisional Patent Application No. 62/525,034, filed on Jun. 26, 2017. The entire contents of the before-mentioned patent applications are incorporated by reference as part of the disclosure of this document.

STATEMENT REGARDING FEDERALLY SPONSORED RESEARCH OR DEVELOPMENT

This invention was made with United States Government support awarded by the following agency: National Science Foundation (NSF) Grant No. CMMI 1246800. The United States Government has certain rights in this invention.

TECHNICAL FIELD

The present document relates to nanocomposite coating material and apparatus therefrom, including guidewires for use in medical surgery.

BACKGROUND

Magnetic Resonance Imaging (MRI) guided procedures provide improved visualization of complex cardiac anatomy, real time physiologic information and a reduction in ionizing radiation but requires MRI compatible catheters/guidewires. The state-of-the art MRI compatible catheters and guidewires are typically classified into (i) active, (ii) passive, and (iii) semi-active types. While active catheter types are directly connected to scanners and are then usually equipped with MRI radio frequency (RF) compatible antennae, the issues related to induced current and attendant temperature increase (up to 70° C.) are highly harmful to ultimate biological application. Alternately passive types are susceptible to artifacts and may not be compatible with many pulse sequences used in MRI. The hybrid semi-active types, e.g., with capacitors, inductors and related frequency resonant elements placed as fiducial unconnected markers along the length of the wires are unsatisfactory in performance.

BRIEF SUMMARY

The present document discloses a guidewire device such as devices with improved catheters or guidewire based devices having one or more advantages of greater electromagnetic compatibility and interference shielding, reduced thermal parasitics and heating due to MRI radiation, easier recognizability in the MRI operation, and reusability. Henceforth, the representative example for ease of description will be the guidewire; this technology is intended for devices used in MRI guided non-invasive and invasive surgery. The present document also discloses improved guidewire based devices implemented through the use of a novel carbon nanotube (CNT)-admixture into a polymer matrix to circumvent the issues of existing heating or external power requirements and through the use of the percolation behavior that can be obtained from nanometer sized CNTs.

In some embodiments of the presently disclosed technology, salient features of guidewire technology (such as capability for embedding fiducial markers) are retained, and at the same time, the inherent advantages of enhanced electromagnetic interference (EMI) compatibility from nanostructures (such as carbon nanotubes) are exploited. Such embodiments advantageously apply nanoscience technologies to the construction of guidewire devices.

In some embodiments, the proposed design provides advantages such as lower power levels due to the higher efficiency of electrical and thermal conductivity from large aspect ratio nanostructures, greater reliability due to the presence of polymeric materials, and immunity to ionizing radiation. In some embodiments of the disclosed technology, active elements, such as transistors and memory elements may be incorporated onto the coatings. Also, in some embodiments, higher device speeds and larger current drives are also ensured by tuning the nanotube content in the guidewire coating. Further, in some embodiments, carbon morphologies are also susceptible to nano-engineering of their geometry, through growth and in situ modification, and offer the possibility of varying device characteristics individually.

The disclosed technology in some embodiments relates to an embedded memory device comprising at least one nanotube/nanowire/nanocone/nanofiber. In at least some further embodiments, the nanotube is a carbon nanotube, and/or more than one nanotube/nanowire/nanocone/nanofiber is employed.

DETAILED DESCRIPTION

Although many useful guidewires already exist, the evolution of a variety of technologies (including, for example, nanomaterial and related composite technologies) continues to drive a need for improved guidewire and catheter based devices that are improved on a number of counts and comprises the modalities of our technology. The related embodiments aim to tackle many of the prevalent issues in many of such catheter/guidewire types through optimized nanocomposite coatings. The enhanced electrical and thermal conductivity of the involved coatings coupled with an optimal thickness of the coatings is expected to significantly reduce the pernicious thermal effects, prevalent in state-of-the art catheters/guidewires and minimize/drastically diminish any temperature rise. In addition to boosting the electromagnetic interference (EMI) shielding of the wires. Some embodiments of the disclosed technology can achieve good shielding (e.g., >60 dB) through such coatings, with the implication that the 20 kW RF power sourced in MRI related machinery could be reduced a million-fold, to 20 mW, which is well within the acceptable specific absorption rate (SAR) guidelines.

The enhanced efficacy of various embodiments of the disclosed technology is in comparison with the active, passive, and semi-active technologies prevalent in catheter/guidewire technologies.

Figure 1B:
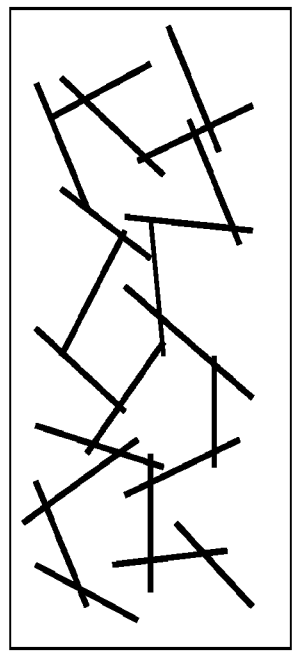
FIG. 1B is a schematic view of oblong shape filler composite (e.g., carbon fiber, nanotube).
Figure 1A:
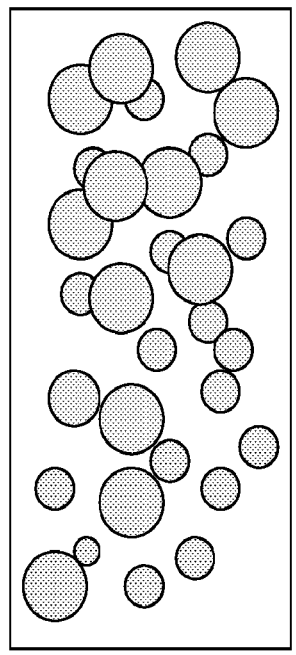
FIG. 1A is a schematic view of spherical shape filler composite (e.g., carbon black)

FIG. 1A is a schematic view of spherical shape filler composite (e.g., carbon black), and FIG. 1B is a schematic view of oblong shape filler composite (e.g., carbon fiber, nanotube). While polymer composites containing conducting fillers such as carbon black, carbon fiber, and metal fiber have previously been extensively investigated for multifunctional applications incorporating structural reinforcement, electromagnetic interference (EMI) shielding, electronic packaging, radar absorbing materials, etc., there has been a limit to the impregnation of polymers with such traditional filler material due to possible embrittlement beyond a certain loading. Consequently, such composites do not have adequate electrical and thermal conductivity as well as EMI characteristics suitable for widespread usage. Moreover, it is easier and advantageous to encompass a composite with linear fillers compared to spherical fillers, as is being done presently.

Innovative materials development resulted in the use of high length to diameter aspect ratio (A.R.) fillers, which favor reinforcement and electrical properties/percolation at lower volume fractions. Some embodiments disclosed herein use carbon nanotubes (CNTs), which offer a most attractive option for a polymer filler. This is primarily due to their extremely large A.R.—which could be as high as $10^6$, e.g., with a 1 micrometer length and 1 nm diameter, coupled with a large interfacial area >1300 m²/g, with the implication of load transfer over a longer length incorporating superior shear strength. Additionally, the CNT surfaces and interfaces can be functionalized and made to interact suitably with the polymer matrix groups using suitable coupling agents for biocompatibility.

It would therefore be advantageous if new technologies could be developed for constructing/operating improved guidewires and related devices. In at least some embodiments of the disclosed technology, the guidewires and related devices have greater immunity to pernicious thermal effects, take on a smaller size, and/or have greater packing densities than conventional devices. In at least some embodiments, the guidewires and related devices may operate with less power and heat dissipation than conventional devices. Such features would be useful in a variety of different types of devices including, for example, catheter based devices.

Carbon nanotubes (CNTs) display exceptional mechanical, chemical and thermal stability, and extensive research is being carried out to probe their electrical properties. Carbon nanotubes, due to their size and shape, can have high aspect ratios (e.g., high length/diameter ratios), and consequently are capable of having a higher efficiency of field emission (e.g., higher current densities given the same or smaller applied voltages), which can be exploited for coating technologies, with minimal incorporation of nanostructure filler. Metallic carbon nanostructures, in various morphologies, i.e., fibers, cones, etc., with a range of diameters (1 nm-100 nm) and lengths (10 nm-100 μm), can be fabricated through Chemical Vapor Deposition (CVD) and other synthesis techniques. Ultrasonication, or electric and magnetic fields can be used to orient the nanotubes in the polymeric material.

Some embodiments of the disclosed technology may be implemented by using a stochastic analysis based excluded volume model to estimate the theoretical critical volume percolation threshold, $\phi_c$ of the CNTs embedded in a polymer matrix, as a function of their length (L), diameter (D), and aspect ratio (A.R.=L/D). For a percolation threshold corresponding to the connectivity of $N_c$ CNTs, and $V_{ex}$ defined as the excluded volume (the space circumscribed around the CNT by the center of another CNT, whereby both CNTs contact each other but do not overlap), the expected values are:

$$E[V_{ex}] = \frac{4\pi}{3}D^3 + 2\pi D^2 E[L] + \frac{\pi}{2}DE[L^2] \quad (1)$$

where E[ ] is the expectation of the relevant quantity. Monte-Carlo simulations may be used to estimate $E[V_{ex}]N_c$ as ~1.4. In this way, an upper bound may be obtained when the lengths vary randomly, and for a given D, the theoretical $\phi_c$ may be determined to be:

$$\phi_c(L) = \frac{E[V_{ex}]N_c}{\frac{4\pi}{3}D^3 + 2\pi D^2 E[L] + \frac{\pi}{2}DE[L^2]} \left(\frac{\pi}{6}D^3 + \frac{\pi}{4}D^2 E[L]\right) \quad (2)$$

The minimal concentration of carbon nanotubes (CNTs) necessary to form a percolating network is analyzed. From a practical perspective, CNT networks have been proposed as constituents of thin film transistors for electronics and biosensors, polymer composites for electromagnetic interference shielding, etc. While variability in device characteristics may be considered, the widespread unpredictability in the intrinsic geometry, e.g., the length (L) of the CNTs, has not yet been modeled. Such issues with predictability of the geometry are typical of nanostructure synthesis processes and could strongly influence the electrical characteristics and device properties. The prediction of a threshold is also pertinent in the synthesis of CNT based composites, where the cost of the nanostructures is a major factor.

An excluded volume percolation theory based model may be used to estimate the theoretical critical volume percolation threshold, $\phi_c$ of the CNTs, as a function of L. For this, it is assumed that the $i^{th}$ CNT has a volume, $v_i$, in a polymer/insulating matrix of unit volume. Now, if the percolation threshold corresponds to the connectivity of $N_c$ CNTs, then the odds of not selecting any CNT (corresponding to a point in the matrix) would be:

$$(1 - \phi_c) = (1 - v_1)\left(\frac{1 - v_1 - v_2}{1 - v_1}\right) \times \quad (3)$$
$$\left(\frac{1 - v_1 - v_2 - v_3}{1 - v_1 - v_2}\right) \ldots \left(\frac{1 - v_1 - v_2 - v_{N_c}}{1 - v_1 - v_2 - \ldots v_{N_c-1}}\right)$$
$$= 1 - N_c \sum_{i=1}^{N_c} \frac{v_i}{N_c}$$

implying that $$\phi_c = N_c E[v] \quad (4)$$

where E[v] denotes the expected value or ensemble average of the CNT volume. It is to be noted that Eq. (4) is distinct compared to the critical percolation threshold extant in literature, which assumes that the percolating objects are penetrable, i.e., hitherto applied to pores in rock, etc. In deriving Eq. (4), it is assumed that the CNTs may be impenetrable. Using the identity, $E[v]=(E[V_{ex}]N_c/E[V_{ex}])(E[v]/N_c)$, where $V_{ex}$ is defined as the excluded volume, the space circumscribed around the CNT by the center of another CNT causes both CNTs to contact each other but do not overlap. For isotropically oriented, spherically capped stick like objects of diameter "D" and random length "L," which are akin to CNTs, as expressed by Eq. (1). Also, for the CNT modeled as a capped cylinder, $E[v]=(\pi/6)D^3+(\pi/4)D^2E[L]$. Note that the CNT diameter is assumed to be constant. For infinitely thin cylinders of deterministic length, Monte Carlo simulations may be used to estimate $E[V_{ex}]N_c$ as ~1.4. This is an upper bound when the lengths vary randomly, as $E[V_{ex}]$ should be weighted to favor the longer CNTs. For a given D, the theoretical $\phi_c$ would be express by Eq. (2).

Figure 2:
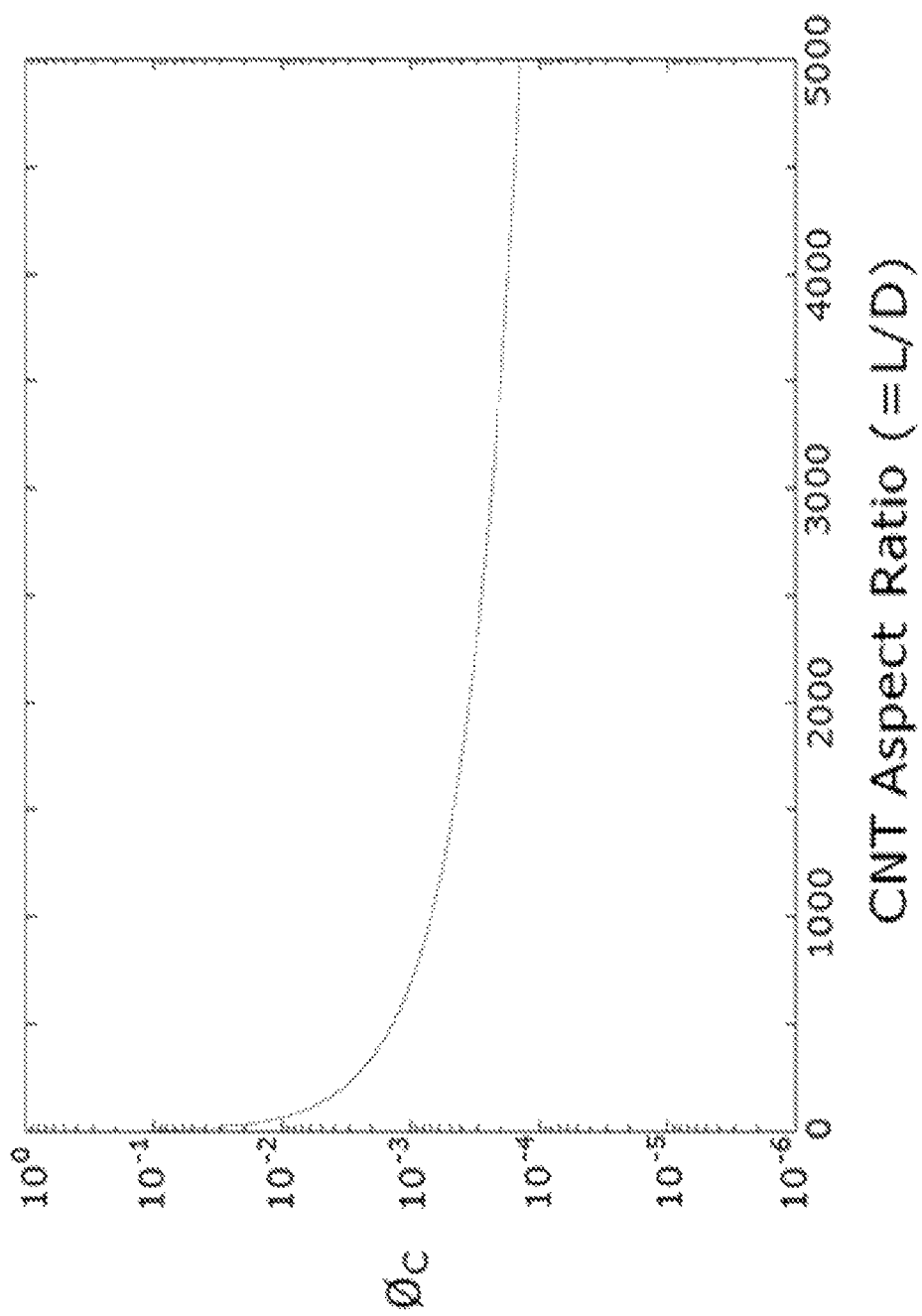
FIG. 2 depicts the variation of the minimum volume fraction ($\phi_c$) with a nanowire/nanotube length/diameter aspect ratio.

FIG. 2 depicts the variation of the minimum volume fraction ($\phi_c$) with a nanowire/nanotube length/diameter aspect ratio. As plotted in FIG. 2, 0.1 volume % of the CNT filler is adequate to get percolation/connectivity of the CNTs (with an A.R. of ~1000) within a polymer matrix and provide enhanced electrical and thermal conductivity for enhanced electromagnetic interference shielding and reduced thermal parasitic effects. In some carbon-polymer composites, it is often found useful to incorporate 20 volume % of carbon black spheres to obtain similar conductivity values.

The large length to diameter aspect ratio of one dimensional nanostructures such as carbon nanotubes (CNTs) or nanowires is expected to enhance both the electrical conductivity ($\sigma$) and thermal conductivity ($\kappa$) of relatively insulating matrices, e.g., polymers, at relatively low nanostructure filler fractions. Integral to such possible enhancement are (i) the postulated high conductivity of the nanostructures, along the length of the wires, due to the reduced scattering space/probability, and (ii) that the fillers span/percolate through the matrix. Moreover, it would be expected that the anisotropy in the $\sigma$ and the $\kappa$ of the fillers would be transferred to the composite and the study of concomitant effects together with aspects related thermal percolation. Our foundational work has wide implications to a wide variety of envisaged applications of nanostructure/polymer composites incorporating structural reinforcement, electromagnetic interference (EMI) shielding, reduced thermal parasitic effects, etc.

For a deterministic L, the variation in $\phi_c$ is shown as a function of the aspect ratio (=L/D). Such a depiction necessarily implies that a definitive $\phi_c$ is obtained at a given L. However, it is commonly observed that L is not a deterministic constant but should properly be considered a random variable, i.e., as $\underline{L}$, that could have considerable variation. For example, it is measured subsequent to ultrasonication—a procedure necessary for dispersion of the CNTs into polymer matrices, that single-walled CNTs (SWNTs) have lengths ranging from 2.2-7.8 µm while multiwalled CNTs (MWNTs) vary in length from 3.0-8.4 µm. In another instance, a batch of SWNTs synthesized through arc-based methods had L in the 0.7-4.3 µm range. Such large variability clearly makes $\phi_c$ a function of $\underline{L}$ and would lead to uncertainties in obtaining an accurate percolation threshold.

The above issues also imply that a suitable stochastic model is necessary to evaluate the $\phi_c$ e.g., for a CNT/polymer composite or a CNT network transistor, as $\phi_c(\underline{L})$ is not equal to the $\phi_c$ evaluated at the average CNT ensemble length, i.e., $\phi_c$ (E[L]). A proper expression for $\phi_c$ would account for variations in $\underline{L}$ and could be expressed through the correlation, i.e., $E[\underline{L}^2]$. The stochastic approach would then provide a theoretical value, i.e., a $\phi_c$ ($\underline{L}$) that accounts for the mean and variance of $\underline{L}$. A theoretical value for $\phi_c$ can be found from Eq. (2) where the average CNT length is now E[L] with a variance, $VAR[\underline{L}]=E[(\underline{L}-E[\underline{L}])^2]=E[\underline{L}^2]-(E[\underline{L}])^2$. Both E[L] and $E[\underline{L}^2]$ can be evaluated by fitting empirical CNT length data to a probability density function (PDF). As the PDF cannot be a priori determined, the sample mean length $\mu_L$ and sample variance $s_L^2$ can be used as unbiased estimates of the population mean and variance.

For the practical application of the above principles and experimental verification, carboxyl (—COOH) group functionalized SWNTs and MWNTs are dispersed into a polymer. A reactive ethylene terpolymer (RET) including an epoxy functional group may be chosen for a polymer/insulating matrix, with the underlying rationale that the epoxide ring rupture on the RET would be facilitated by the —COOH groups on the functionalized CNTs. The bonding between the —COOH and the epoxide group could help in the uniform dispersion. The exact location of the functional groups would depend on the defect density on the CNTs and can be manipulated. However, if the defects are considered to be randomly dispersed, isotropic bonding of the CNTs with the polymer matrix is implied and yields uniform mixing.

Figure 3A:
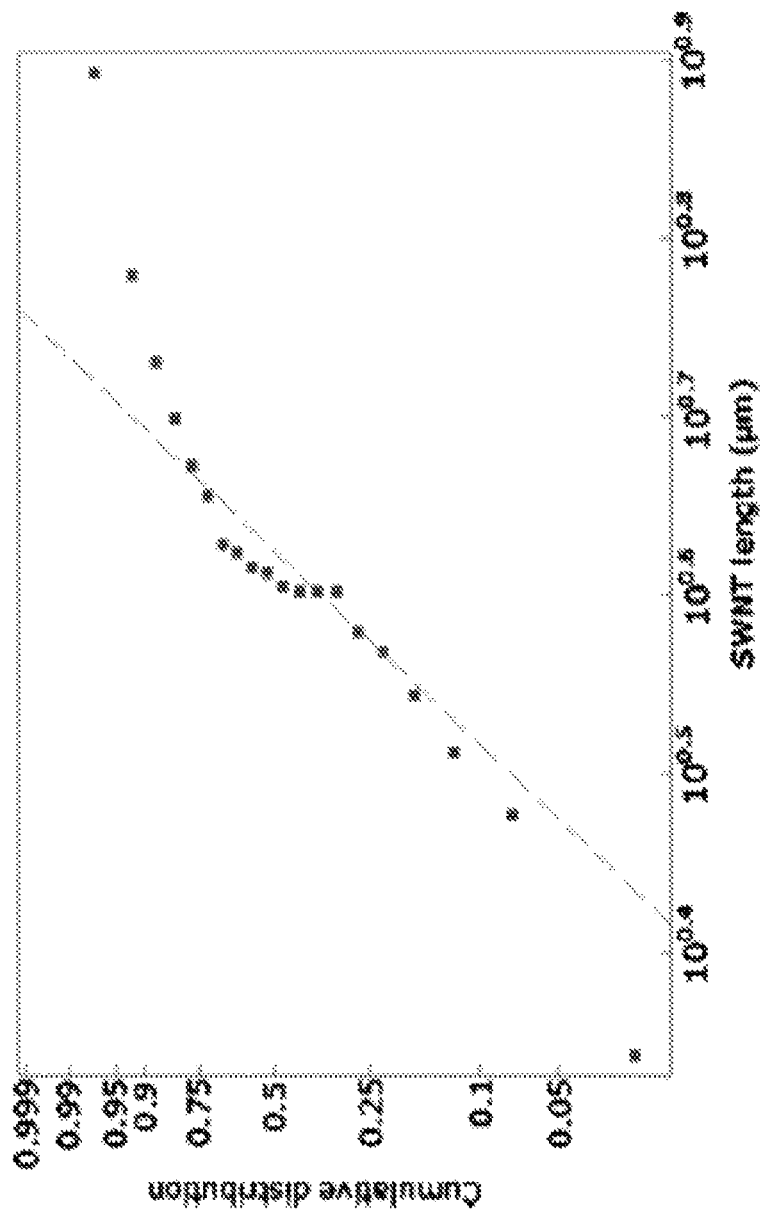
FIG. 3A shows the lengths of single-walled carbon nanotubes (SWNTs)
Figure 3B:
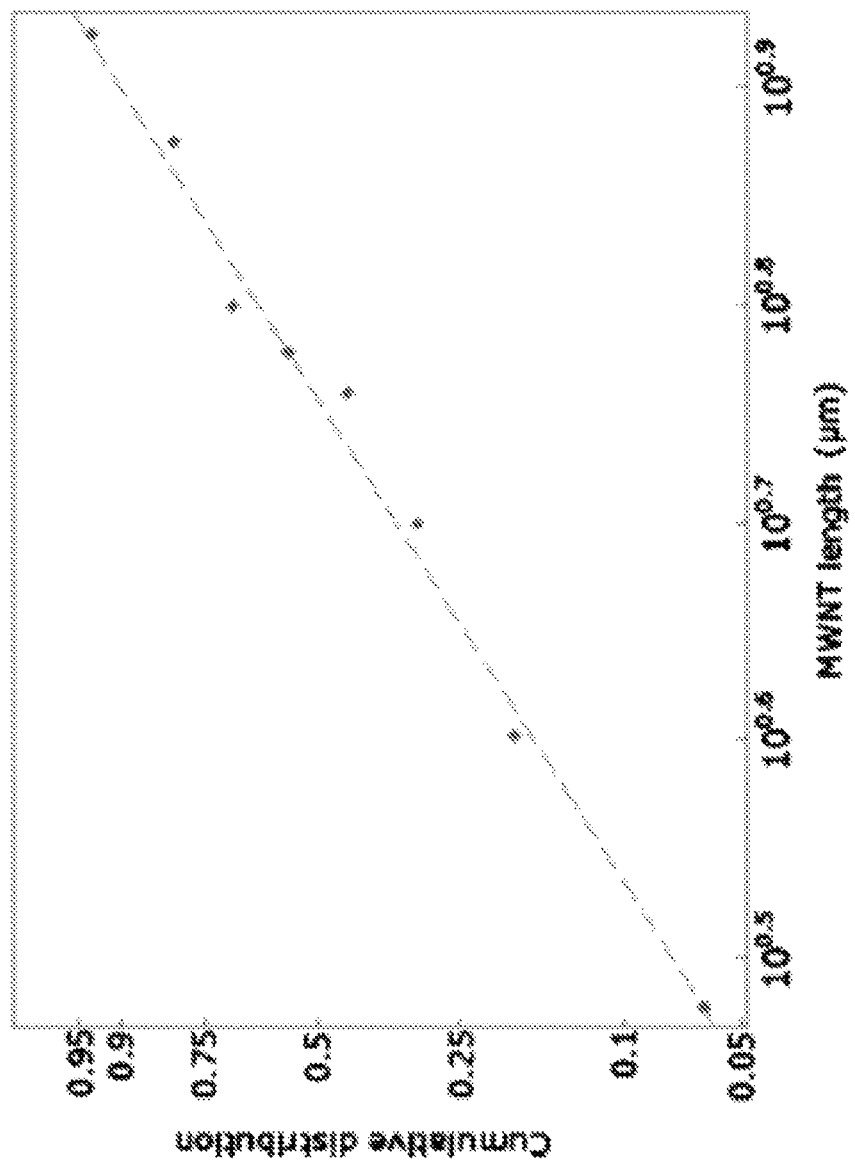
FIG. 3B shows multiwalled carbon nanotubes (MWNTs) dispersed into the polymer matrix in an embodiment of the disclosed technology.
Figure 3C:
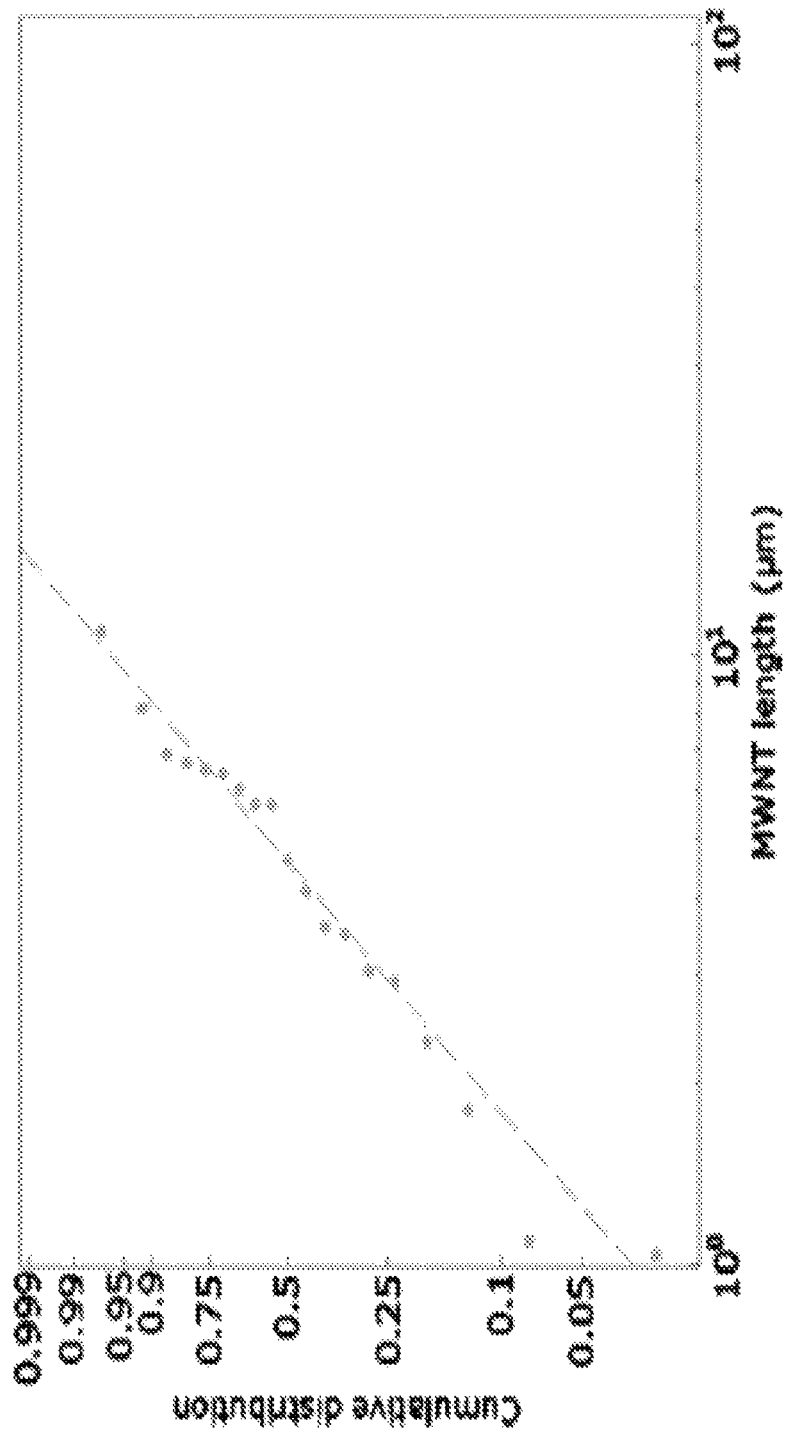
FIG. 3C shows MWNTs from another comparable example.

FIG. 3A shows the lengths of single-walled carbon nanotubes (SWNTs), FIG. 3B shows multiwalled carbon nanotubes (MWNTs) dispersed into the polymer matrix in an embodiment of the disclosed technology, and FIG. 3C shows MWNTs from another comparable example. Nonlinearities in FIG. 3A indicate a poor fit to a Weibull while excellent fits were obtained for FIG. 3B and FIG. 3C.

The lengths of the CNTs in several composite samples may be first measured using a scanning electron microscope. In the case of SWNTs, while the bundle diameters (D) may be noted to be about 4.8 nm using atomic force microscopy, the length variation did not fit Gaussian, exponential, Rayleigh, log-normal, or Weibull FIG. 3A, distributions. The poor fit is attributed to a mixture of different PDFs of the SWNT lengths within the composite. Then, mean sample SWNT length ($\mu_L$~4.28 μm) may be used as an estimate of E[$L$] and the sample variance of $s_L^2$~1.364 μm² for estimating E[$L^2$](=VAR[$L$]+E[$L$]²~$s_L^2+\mu_L^2$). Using the upper bound of $N_cE[V_{ex}]$, ~1.4, and substituting sample statistics, $\mu_L$ and $s_L^2$ in Eqs. (2) and (4) yields a theoretical percolation threshold of $\phi_c$ ($L$)=0.000 73 .

On the other hand, for the case of MWNT bundles (with D~188 nm) the lengths may be fit very satisfactorily to a Weibull distribution shown in FIG. 3B. For example, the value of the correlation coefficient for the MWNT lengths, $r^2$ (=0.9833), exceeds the tenth percentile of $r^2$ (=0.85) established from Monte Carlo simulations using random numbers known to fit a Weibull distribution. In addition, the MWNT length data in FIG. 3C shows a satisfactory fit to a Weibull distribution.

Generally, the $n^{th}$ moment for a Weibull distribution is given by E[$L^n$], where $$E[L^n] = \theta^n \Gamma\left(\frac{n}{\beta} + 1\right), \quad (5)$$

Γ denotes the Gamma function. A two parameter Weibull PDF is then completely described by a shape parameter, β and the scale parameter θ. For FIG. 3B, β=3.97 and θ=6.3525 may be calculated from the slope and intercept and may then be used to find the statistical moments, e.g., mean, correlation, skewness, kurtosis, etc., of the Weibull distribution. To interpret these numbers, it is noted that for β=3.6, the distribution of lengths would be symmetrical about the mean. A β>3.6 implies a left-hand skewness of the MWNT length PDF, i.e., more CNTs are shorter rather than longer, while a β<3.6 suggests the MWNT lengths have a right-hand skewed distribution. Furthermore, θ denotes the value below which about 63% of the NT lengths are smaller, i.e., about 63% of the CNT lengths are less than 6.3525 μm. Additionally, a high $r^2$ on a Weibull plot suggests that the length distributions arise from a single PDF instead of a mixture of different PDFs. An $r^2$ of about 0.9833, in FIG. 3B, then suggests that a single, particular mechanism could determine the length distribution, e.g., a uniform mode of fracture at particular defects, due to the CNT processing. A poor fit, as with the SWNT lengths in FIG. 3A, would indicate that the length distribution arises from a mixture of two or more distributions where each distribution is the outcome or consequence of a different event, e.g., CNT fracture could occur at both defect-prone and defect-free sites, or could be mediated through multiple varieties of defects.

From the calculation of the moments, for the case of FIG. 3B with MWNTs, $\mu_L$ may be 5.756 μm, and $s_L^2$ may be 2.643 μm². The substitution of these $\mu_L$ and $s_L^2$ values into Eq. (2) then yields a theoretical $\phi_c$ ($L$)=0.0193.

Figures 4A, 4B:
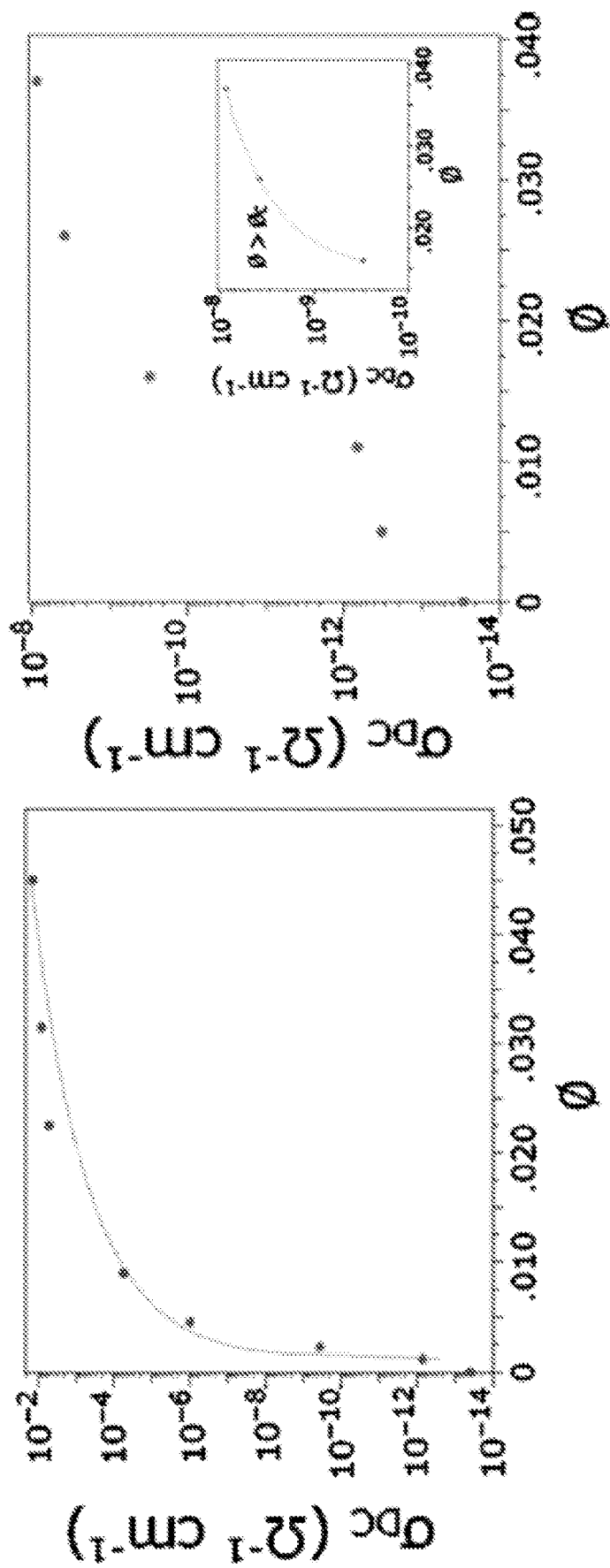
FIG. 4A shows the variation in dc electrical conductivity ($\sigma_{dc}$) with volume fraction ($\phi$) for SWNTs dispersed in a polymer matrix.
FIG. 4B shows the variation in dc electrical conductivity ($\sigma_{dc}$) with volume fraction ($\phi$) for MWNTs dispersed in a polymer matrix.

FIG. 4A shows the variation in dc electrical conductivity ($\sigma_{dc}$) with volume fraction (φ) for SWNTs dispersed in a polymer matrix, and FIG. 4B shows the variation in dc electrical conductivity ($\sigma_{dc}$) with volume fraction (φ) for MWNTs dispersed in a polymer matrix. The inset in FIG. 4B indicates the fit of $\sigma_{dc}$ to an expression of the form $\sigma_{dc} \Box \sigma_0 (\phi-\phi_c)^t$ for $\phi > \phi_c$.

To experimentally analyze and correlate the influence of statistical variation on electrical percolation thresholds, the electrical conductivity is measured; σ. A four-point probe may be used to measure the electrical resistance, R, for composites with R<1 GΩ, using a picoammeter and a sourcemeter. For higher resistance (>1 GΩ) composites, two point measurements using a semiconductor device analyzer with triaxial probes may be employed. For these measurements, samples with sputtered gold contacts may be used. The experimental $\phi_c$ for electrical percolation may then be determined by fitting the measured σ of the CNT dispersed composites to the conductivity power law equation, $\sigma = \sigma_0 (\phi-\phi_c)^t$. Subsequently, for the SWNT samples shown in FIG. 4A, from the fit to the a variation, a $\phi_c$ of 0.0011, which is quite close to the theoretical mean (~0.000 73), is obtained. In the case of MWNT dispersed polymers, the $\phi_c$ may be found to be 0.0147 which, is again close to the theoretical mean of ~0.0193, predicted from stochastic theory.

As discussed above, statistical analysis using a stochastic approach can be used to describe the impact of random CNT lengths on the electrical percolation thresholds. Such modeling could be used to determine the thresholds while accounting for realistic process variability. The proposed methodology can be extended to other mutable CNT characteristics such as diameter, agglomeration, curvature, etc.

Figure 5B:
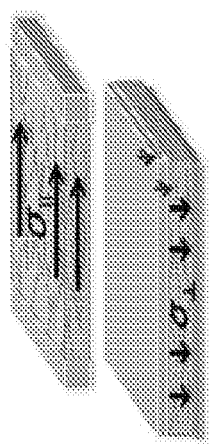
FIG. 5B is a schematic diagram showing that in-plane (top) and cross-plane (bottom) electrical and thermal conductivity measurements may be carried out to ascertain anisotropy and percolation.
Figure 5A:
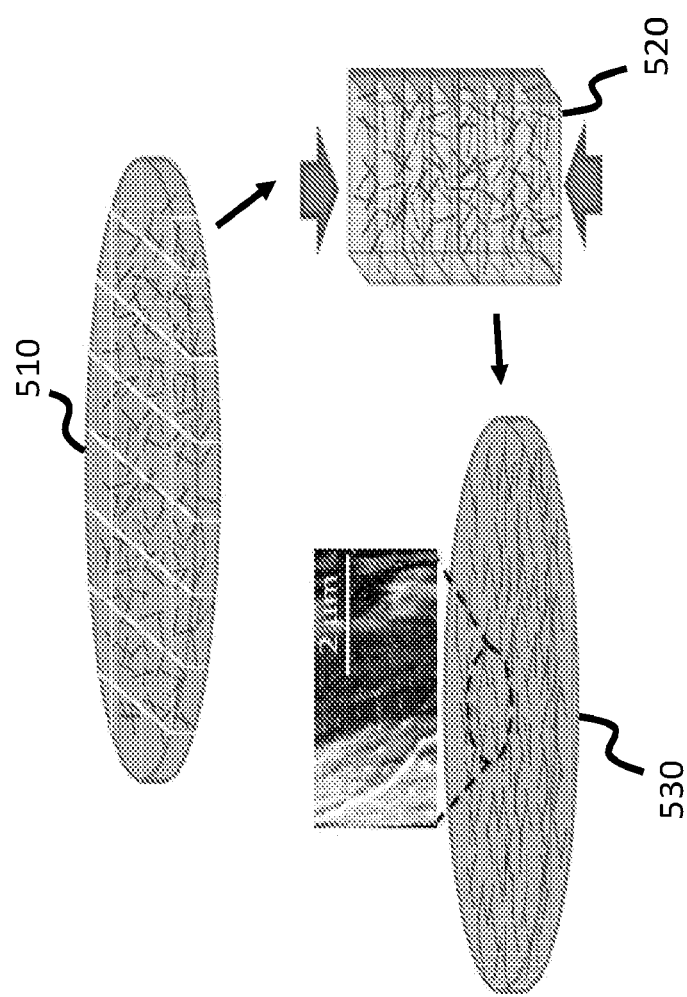
FIG. 5A shows a schematic diagram illustrating an example embodiment of synthesis of the nanocomposite material inducing anisotropy of the electrical and thermal conductivity, through repeated compressive stress, showing that the compressed sheet comprises nanotubes preferentially aligned in the plane of the sheet.

FIG. 5A shows a schematic diagram illustrating an example embodiment of synthesis of the nanocomposite material inducing anisotropy of the electrical and thermal conductivity, through repeated compressive stress, showing that the compressed sheet comprises nanotubes preferentially aligned in the plane of the sheet, and FIG. 5B is a schematic diagram showing that in-plane (top) and cross-plane (bottom) electrical and thermal conductivity measurements may be carried out to ascertain anisotropy and percolation. In an embodiment of the disclosed technology, the composite may be fabricated for coating surfaces through a mechanical compression process. In another embodiment of the disclosed technology, the compressed sheet comprises nanotubes preferentially aligned in the plane of the sheet.

The large length to diameter aspect ratio of one dimensional nanostructures such as carbon nanotubes (CNTs) or nanowires is expected to enhance both the electrical conductivity (σ) and thermal conductivity (κ) of insulating matrices, e.g., polymers, at relatively low nanostructure filler fractions. Integral to such possible enhancement are (i) the postulated high conductivity of the nanostructures along the length of the wires, due to the reduced scattering space/probability, and (ii) the aspect that the fillers span/percolate the matrix. Moreover, it would be expected that the anisotropy in the σ and the κ of the fillers would be transferred to the composite, and concomitant effects, together with issues related to thermal percolation, are discussed here. Such investigations would have wide implications to a wide variety of envisaged applications of nanostructure/polymer composites incorporating structural reinforcement, electromagnetic interference (EMI) shielding, electrochemical capacitors, etc.

Multi-walled CNTs (of average length 1.6 μm and diameter of 45 nm, with standard deviations of 0.5 μm and 14 nm, respectively, yielding an average length/diameter aspect ratio—A.R., of ~35) in a range of volume fractions ($\phi$), i.e., 1-10 vol. % (higher fractions rendered the composites brittle) may be dispersed uniformly in a reactive ethylene terpolymer (RET) matrix through a careful blend of solution processing and mixing techniques, for example, through various steps 510, 520, and 530 in FIG. 5A. The uniformity of the dispersion may be gauged through considering the nanostructure dispersion, through scanning electron microscopy (SEM) micrographs at various length scales (1 μm-100 μm), as well as through the development and use of an image processing algorithm for comparing the given distribution to a preferred (e.g., uniform) distribution. The underlying rationale for the choice of the RET is that ester bond linkages between the carboxyl groups on acid functionalized CNTs and the epoxide groups on the polymer may enable robust bonding, and may be verified through Fourier transform infrared (FTIR) spectroscopy. Consequently, both functionalized CNTs and RET may be solubilized in toluene solvent and blended through ultrasonication. The blend may be cast into a glass Petri dish, where the excess solvent may be removed by heat treatment in a furnace. The obtained composite may be removed from the dish and then stacked and subject to a hot press treatment to obtain CNT/RET films/plates of the desired thickness. The electrical and thermal measurements on representative composite plates may have about 2 mm thickness.

Four probe measurements may be used for the $\sigma(=x/RA$, evaluated from the measured electrical resistance R, with x as the contact spacing and A as the cross-sectional area) of the composites with R<1 GΩ, while for higher resistance composites two-point measurements (using a semiconductor device analyzer with triaxial probes) may be employed. The composites may be subject to mild oxygen plasma treatment to remove surface contamination and subsequently, 5-10 nm of Ti followed by 100 nm of Au may be sputtered on for electrical contacts. For measurements of the in-plane conductivity ($\sigma_\square$), the contacts may be on the either side of the composite, while measurements of the cross-plane (/through thickness) conductivity ($\sigma_\perp$) used contacts deposited on the top and bottom of the composite, as shown in FIG. 5B. Self-heating may be negligible due to the low applied power.

Figure 6:
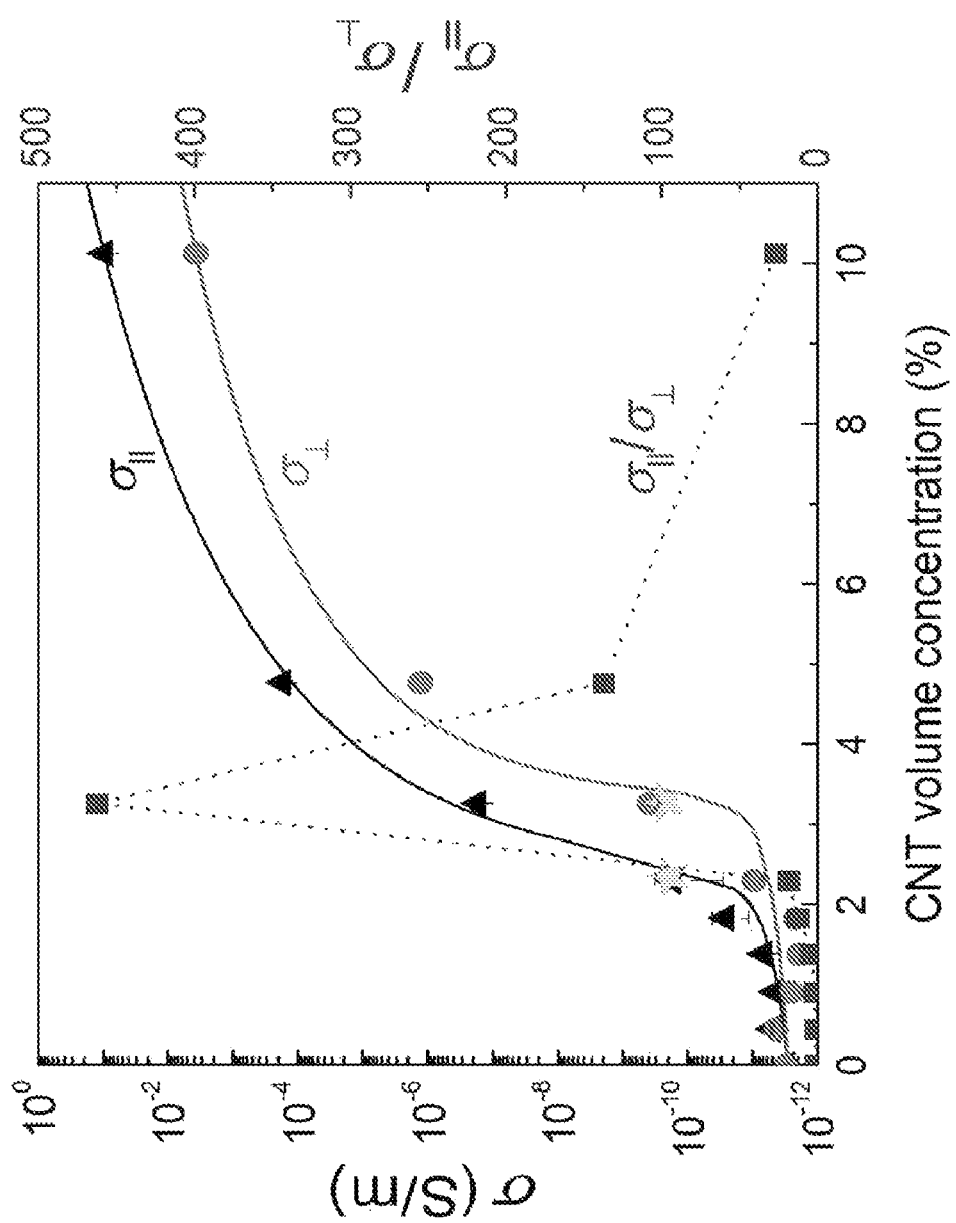
FIG. 6 depicts the variation of the measured electrical conductivity with added CNT filler concentration depicted for the in plane ($\sigma_{//}$) and cross plane ($\sigma_\perp$) configurations. The anisotropy ratio, i.e., $\sigma_{//}/\sigma_\perp$ is indicated on the right-hand axis.

FIG. 6 depicts the variation of the measured electrical conductivity with added CNT filler concentration depicted for the in plane ($\sigma_{II}$) and cross plane ($\sigma_\perp$) configurations. The anisotropy ratio, i.e., $\sigma_{II}/\sigma_\perp$ is indicated on the right-hand axis. The star mark indicates the results of the Straley model relating the product of the electrical resistances of the matrix and the filler to the percolation threshold. For measurements of the in-plane conductivity ($\sigma_{II}$), the contacts may be on the either side of the composite, while measurements of the cross-plane (/through thickness) conductivity ($\sigma_\perp$) used contacts deposited on the top and bottom of the composite. Self-heating may be negligible due to the low applied power. The measured $\sigma_{II}$ and $\sigma_\perp$ as a function of the CNT concentration is plotted in FIG. 6.

The variation of both $\sigma_{II}$ and $\sigma_\perp$ could be fitted to power law relations of the form:

$$\sigma_{DC} \sim \begin{cases} (\phi_c - \phi)^{-s}, & \phi < \phi_c \\ (\phi - \phi_c)^t, & \phi > \phi_c \end{cases} \quad (6)$$

where $\phi_c$ is the threshold volume fraction for electrical percolation, while s and t are critical exponents. From excluded volume percolation theory, it may be estimated that for CNTs with an aspect ratio (A.R.) of ~35, a $\phi_c$ of ~2.2 volume %, in agreement with experiment. The differing values of $\phi_c$ for the $\sigma_\perp$ and $\sigma_{II}$ indicate anisotropy and the $\sigma_{II}/\sigma_\perp$ ratio could be tentatively understood from the greater deviation from isotropic arrangement of the nanotubes. An estimation can be made, the threshold from excluded volume percolation theory, for CNTs with an aspect ratio (A.R.) of ~35, using $$\phi_c(A.R.) = \frac{C}{\frac{4\pi}{3} + 2\pi(A.R.) + \frac{\pi}{2}(A.R.)^2} \left[\frac{\pi}{6} + \frac{\pi}{4}(A.R.)\right]. \quad (7)$$

where C is a constant in the range of 1.4 (for thin rods) to 2.8 (for spherical objects). Using C~1.4, for the nanotubes, a $\phi_c$ of ~2.2 vol. % may be estimated. While the fitted $\phi_c$ is ~2.3 vol. % for the $\sigma_\square$ change, a value of ~3.3 vol. % may be noted for the $\sigma_\perp$ variation. Moreover, there may be a more gradual (t~4.2 for $\sigma_\perp$ compared with a t value ~5.7 for the $\sigma_\square$ variation) and smaller net increase. The differing values of $\phi_c$ for the $\sigma_\perp$ and $\sigma_\square$ indicate anisotropy and the $\sigma_\square/\sigma_\perp$ ratio has been indicated in FIG. 6, e.g., the larger value for $\sigma_\perp$ could be tentatively understood from the greater deviation from isotropic arrangement of the nanotubes.

Figure 7:
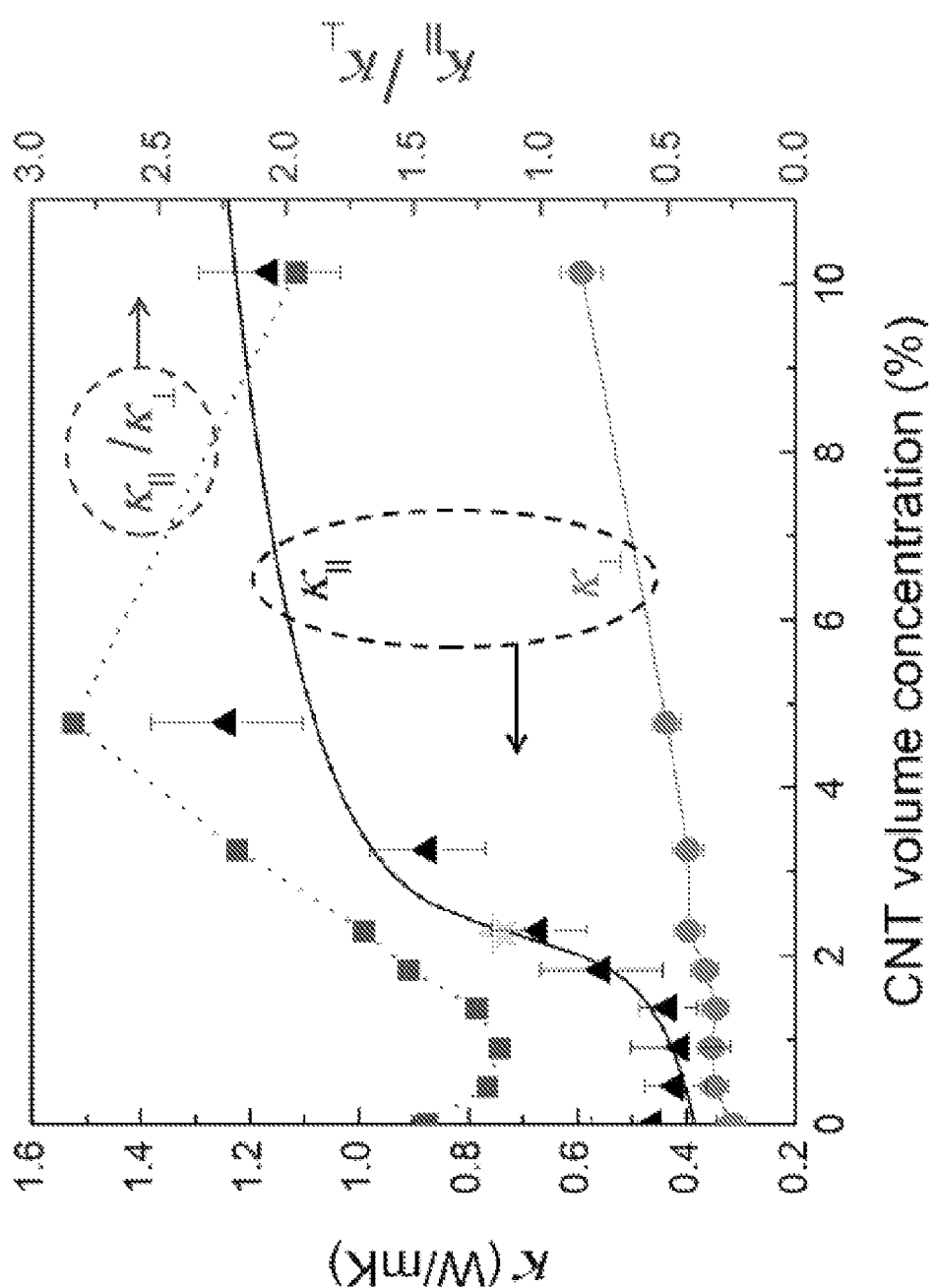
FIG. 7 depicts the variation of the measured thermal conductivity with added CNT filler concentration depicted for the in plane ($\kappa_{//}$) and cross plane ($\kappa_\perp$) configurations. The anisotropy ratio, i.e., $\kappa_{//}/\kappa_\perp$ is indicated on the right-hand axis.

FIG. 7 depicts the variation of the measured thermal conductivity with added CNT filler concentration depicted for the in plane ($\kappa_{II}$) and cross plane ($\kappa_\perp$) configurations. The anisotropy ratio, i.e., $\kappa_{II}/\kappa_\perp$ is indicated on the right-hand axis. The star mark indicates the results of a Straley model relating the product of the thermal resistances of the matrix and the filler to the percolation threshold. The cross plane ($\kappa_\perp$) and in-plane ($\kappa_{II}$) thermal conductivity values may be measured and plotted as a function of the CNT concentration in FIG. 7, along with the $\kappa_{II}/\kappa_\perp$ anisotropy ratio. While a fairly linear change may be noted for $\kappa_\perp$, a percolation like behavior, similar to the variation in $\sigma$, may be observed in $\kappa_{II}$. The $\kappa_{II}$ variation may be expressed as:

$$\kappa_{\|} \sim \begin{cases} (\phi_{c,k} - \phi)^{-p}, & \phi < \phi_{c,k} \\ (\phi - \phi_{c,k})^q, & \phi > \phi_{c,k} \end{cases} \quad (8)$$

where, $\phi_c$ is now the threshold volume fraction for the onset of thermal percolation, and p and q are critical exponents in the respective regimes. Here, a $\phi_{c,k}$~2.2 vol %, close to the theoretically expected value, with p~0.2 and q~0.1 experimentally obtained. The value of the exponents in the power laws depends on the particular type of conductivity (i.e., electrical or thermal) as well as on the ratio of the respective conductivities of the constituent phases.

Concomitantly, the cross plane ($\kappa_\perp$) and in-plane ($\kappa_\square$) thermal conductivity values may be estimated through a steady state method and the 3ω methodology, respectively. For $\kappa_\perp$ the experimental apparatus may be modeled and constructed in accordance with ASTM (American Society for Testing and Materials) standards E1225 and D 5470. The accuracy of measurement may be estimated to be about 3% through comparison with standards. For the $\kappa_\square$ measurements, employing the 3ω technique, Ti/Au metal lines (70 μm wide and 10 mm long) which serve as both heater and thermometer may be deposited on the composites, with the length scales chosen so as to approximate a narrow line heat source (with a ratio of the sample thickness to the metal line width of ~30). Using a lock-in amplifier and a Wheatstone bridge setup, alternating current, I(ω), of angular frequency ω (with frequencies (f) in the range of 0.1 Hz-1000 Hz), passed through the metal lines induces resistance oscillations at 2ω:R(2ω), due to Joule heating (~I²R), from which the thermal conductivity can be deduced from the third harmonic voltage, V(3ω) (=I (ω)R(2ω)). The temperature change (ΔT) may be deduced using the relation:

$$\Delta T = \frac{2\ V(3\omega)}{\alpha V(\omega)},$$

where α is the measured temperature coefficient of resistance of the metal line. Assuming an adiabatic boundary condition at the bottom of the composite (which is valid for a thermal penetration depth smaller than 2 mm (Ref 19)), the estimated ΔT could be then related to the thermal conductivity product, $\kappa_\square \cdot \kappa_\perp$, obtained through $$\Delta T \cong \frac{P}{2\pi\sqrt{\kappa_\square \cdot \kappa_\perp}}[-\ln(\omega) + G]. \quad (9)$$

In Eq. (9), P is the electrical power per unit length of the heater and G is a constant. Combining the steady-state and the 3ω measurements, the individual values of $\kappa_\square$ and $\kappa_\perp$ may be computed. Generally, the CNTs are covered by the polymer and the surface of the composites is not electrically conducting. The sample and the metal lines are electrically isolated/mutually insulated at all CNT concentrations through monitoring the electrical capacitance (for possible shorting) as well as through the variation of the temperature change/oscillation (ΔT) with frequency (f). While insulated samples exhibit a well-predicted variation, non-insulated samples (e.g., a bare Si substrate) exhibit irregular behavior.

The measured $\kappa_\perp$ and the estimated $\kappa_\square$ are then plotted as a function of the CNT concentration in FIG. 7 along with the $\kappa_\square/\kappa_\perp$ anisotropy ratio. While a fairly linear change may be noted for $\kappa_\perp$, a percolation like behavior, similar to the variation in σ, may be observed in $\kappa_\square$. Then Eq. (9) can be used to fit the $\kappa_\square$ variation:

$$\kappa_\square \sim \begin{cases} (\phi_{c,k} - \phi)^{-p}, & \phi < \phi_{c,k} \\ (\phi - \phi_{c,k})^q, & \phi > \phi_{c,k} \end{cases}, \quad (10)$$

where, $\phi_{c,k}$ is now the threshold volume fraction for the onset of thermal percolation, and p and q are critical exponents in the respective regimes. Experimentally, a $\phi_{c,k}$~2.2 vol. %, close to the theoretically expected value, with p~0.2 and q~0.1, can be obtained. The value of the exponents in the power laws depends on the particular type of conductivity (i.e., electrical or thermal) as well as on the ratio of the respective conductivities of the constituent phases.

The concomitant larger variation in the increase of the σ (ten-twelve orders of magnitude for $\sigma_\perp$ and $\sigma_\square$) of the CNT/polymer composites compared to the increase of the κ (50% and 400% for $\kappa_\perp$ and $\kappa_\square$, respectively) may be attributed to the intrinsically greater range in electrical conductivity. In the former case, one has to consider the much lower electrical resistance of the CNTs compared to the polymers, while there is generally a much smaller variation in κ between disparate materials. The substantial enhancement in $\kappa_\square$ compared to $\kappa_\perp$ is also to be noted. The $\kappa_\square$ increase may be caused by the effects of percolation. Further evidence may be obtained through adapting a Straley model (used for determining the critical exponents for the conductivity of random resistor lattices), where the filler ($R_f$) and matrix ($R_m$) could be represented as thermal resistors. Through such modeling, the effective thermal conductivity at the percolation threshold fraction could be related to $R_f^u R_m^{1-u}$, where $$u = \frac{p}{p+q},$$

and the estimated value has been indicated through a star mark in FIG. 7. The equivalent σ values, where the filler and the matrix may be represented as electrical resistors, have been indicated through the star mark symbol in FIG. 6.

Figure 8A:
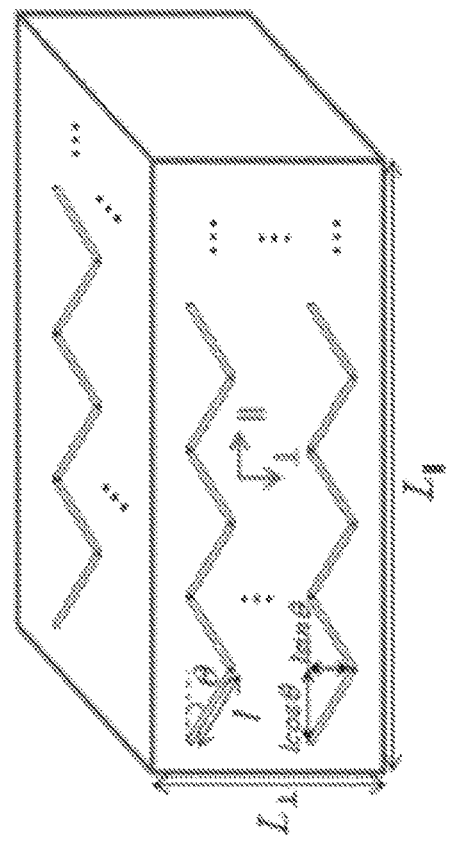
FIG. 8A shows modeling networks of aligned MWNTs in the polymer matrix.
Figure 8B:
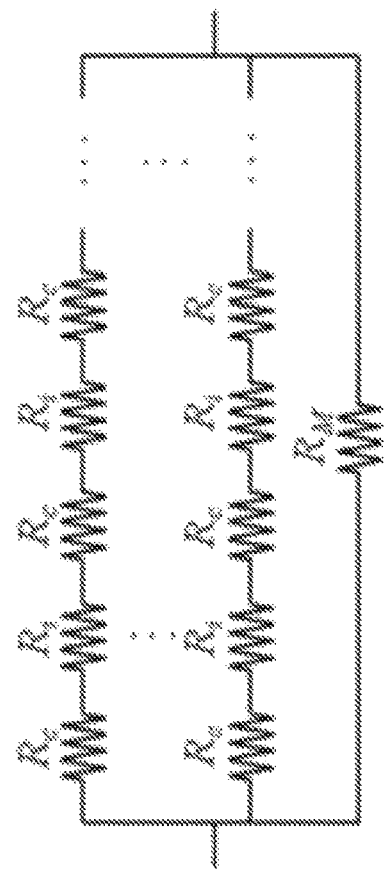
FIG. 8B shows the equivalent electrical/thermal circuit schematic with Rc as the nanotube resistance and Ri as the interfacial resistance.

FIG. 8A shows modeling networks of aligned MWNTs in the polymer matrix, and FIG. 8B shows the equivalent electrical/thermal circuit schematic with Rc as the nanotube resistance and Ri as the interfacial resistance. Connectivity effects encompassing both electrical and thermal conductivity can be modeled through a two-dimensional model considering the total number of percolating networks in the in plane and cross plane directions, contributing to an equivalent resistance, $R_\square$ and $R_\perp$, respectively. Following the schematic in FIGS. 8A and 8B, it is assumed that each network is comprised of a series of nanotubes, and many such networks yield a nanostructure contributed total resistance in the in plane direction ($R_{CNT,\square}$). Conduction would occur simultaneously through the polymer matrix of resistance=$R_{M,\square}$. If the resistance of a single nanotube, $$R_c = \frac{l}{A_c \sigma_c},$$

with l being the average nanotube length, $A_c$ the cross-sectional area, and $\sigma_c$ the conductivity (which should now be interpreted as an electrical: σ or thermal conductivity: κ) with an interfacial resistance, $R_i$ (in units of Ω m²), then $R_{CNT,\square}$ would be $$\frac{1}{R_{CNT,\square}} = \frac{1}{\left(R_c + \frac{R_i\cos(\theta)}{A_c}\right)\frac{L_\square}{l\cos(\theta)}} \frac{N_c l\cos(\theta)}{L_\square}. \quad (11)$$

where θ is an average orientation angle between the CNT longitudinal axis and the horizontal, $L_\square$ is the length of the composite sample, and $N_c$ indicates the total number of CNTs as estimated through the incorporated volume fraction (φ). The second multiplicative term on the right is a measure of the number of horizontal networks. The $$R_{M,\square} = \frac{L_\square}{A_\square(1-\phi)\sigma_m},$$

where $A_\square$ is the composite cross-sectional area and $\sigma_m$ is the matrix (/polymer) conductivity. The net in-plane conductivity ($\sigma_\square$) constituted of $R_{CNT,\square}$ and $R_{M,\square}$ would be $$\sigma_\square = \frac{\phi\cos^2(\theta)}{\left(\frac{1}{\sigma_c} + \frac{R_i\cos(\theta)}{l}\right)} + (1-\phi)\sigma_m. \quad (12)$$

Through similar methodology, the net cross-plane conductivity ($\sigma_\perp$) constituted of $R_{CNT,\perp}$ and $R_{M,\perp}$ would be $$\sigma_\perp = \frac{\phi\sin^2(\theta)}{\left(\frac{1}{\sigma_c} + \frac{R_i\sin(\theta)}{l}\right)} + (1-\phi)\sigma_m. \quad (13)$$

Assuming a range of $\theta$ (i.e., $|\theta|<\theta_b$) and a constraint on the anisotropy ratio between the in-plane and the cross-plane conductivity, i.e., $$\frac{\langle\sigma_\square\rangle}{\langle\sigma_\perp\rangle} \to 1,$$

as $\theta_b \to \pi/2$, Eq. (14) can be derived:

$$\frac{\langle\sigma_\square\rangle}{\langle\sigma_\perp\rangle} = \frac{\theta_b + \sin(\theta_b)\cos(\theta_b) + \left(\frac{1-\phi}{\phi}\right)\left(\frac{1}{\sigma_c} + \frac{2R_i\sin(\theta_b)}{l}\right)\sigma_m}{\theta_b - \sin(\theta_b)\cos(\theta_b) + \left(\frac{1-\phi}{\phi}\right)\left(\frac{1}{\sigma_c} + \frac{2R_i\sin(\theta_b)}{l}\right)\sigma_m}. \quad (14)$$

In the case of electrical conductivity, due to the measured small $\sigma_m$ ($\sim 3\times10^{-12}$ $\Omega^{-1}m^{-1}$), the expressions on the far right hand side of the numerator and denominator can be ignored, and Eq. (15) can be obtained:

$$\frac{\langle\sigma_\square\rangle}{\langle\sigma_\perp\rangle} \cong \frac{\theta_b + \sin(\theta_b) + \cos(\theta_b)}{\theta_b - \sin(\theta_b) + \cos(\theta_b)} \cdot \chi \quad (15)$$

Inserting the corresponding $\sigma_\perp$ and $\sigma_\square$ from FIG. 6, at $\phi>\phi_c$ (i.e., at 3.3 vol. %, 4.8 vol. %, and 10 vol. %), the $\theta_b$ values may be 4.6°, 8.5°, and 19°, respectively. These values may then be used for interpreting the thermal conductivity variation vis-à-vis the percolation like behavior of $\kappa_\square$.

However, for modeling the thermal conductivity anisotropy, $$\frac{\langle\kappa_\square\rangle}{\langle\kappa_\perp\rangle}$$

the matrix conductivity, $\kappa_m$ (~0.3 W/mK) cannot be neglected, and terms involving the thermal interfacial resistance ($R_i^{th}$ in units of $m^2K/W$) would remain $$\frac{\langle\kappa_\square\rangle}{\langle\kappa_\perp\rangle} = \frac{\theta_b + \sin(\theta_b)\cos(\theta_b) + \left(\frac{1-\phi}{\phi}\right)\left(\frac{1}{\kappa_c} + \frac{2R_i^{th}\sin(\theta_b)}{l}\right)\kappa_m}{\theta_b - \sin(\theta_b)\cos(\theta_b) + \left(\frac{1-\phi}{\phi}\right)\left(\frac{1}{\kappa_c} + \frac{2R_i^{th}\sin(\theta_b)}{l}\right)\kappa_m}. \quad (16)$$

Along with the corresponding $\kappa_\square$ and $\kappa_\perp$ from FIG. 7, the $\theta_b$ values obtained previously may be inserted into Eq. (16), to consistently estimate a $\kappa_c$ (~240 W/mK) and an $R_i^{th}$ (~7×10$^{-8}$ m$^2$K/W). Such estimates are in excellent accord with previous evaluations of nanotube interfacial thermal resistance and further indicate a significant modulation of the thermal conductivity of nanostructures, when they are dispersed into a matrix. While a lack of percolation can be observed due to (i) the relatively low thermal conductivity contrast and (ii) the interfacial resistance between the conducting nanostructure and the matrix (polymer), percolation behavior is indeed possible. For example, it may be concluded based on theoretical analysis (based on the finite element method: FEM and molecular dynamics) that the low thermal conductivity contrast (of less than 10$^4$) between the matrix and the filler precludes percolation. A linear variation of the thermal conductivity with volume fraction is predicted based on effective medium theory, which may not be valid at/near the percolation threshold. In an example of single walled nanotube-epoxy composites, the random orientation of the nanotubes may be the reason for the thermal conductivity increase. Indeed, a greater degree of isotropy would imply a lower percolation threshold as indicated in FIG. 6. Various embodiments of the disclosed technology can be implemented considering the effects of interfacial resistance between the nanotubes and the matrix.

Some embodiments of the disclosed technology adapt a synthesis methodology, e.g., using stacking of nanotube/polymer composite sheets, facilitating percolation behavior. An increased nanotube aspect ratio may yield a corresponding exponential increase of the thermal conductivity.

Through detailed experiments and modeling, evidence of anisotropy can be shown in both the electrical and thermal conductivity in nanotube/polymer composites. A power law relation for the thermal conductivity is indicated, indicative of percolation-like behavior, with implications for tunable thermal conductivity and thermal switching.

While carbon based materials, such as carbon black and fibers, have previously been used in polymer composites, their widespread use is limited due to a maximum loading capability, beyond which there is embrittlement. Linear structures, such as carbon nanotubes then, are more attractive candidates for filler materials in composites, primarily due to their large aspect ratio and tunable electrical conductivity, which enables electrical percolation to be achieved with very small amounts of nanotubes. Some embodiments of the disclosed technology may achieve higher values of the electromagnetic interference (EMI) shielding efficiency (SE) at a lower loading fraction of nanotubes (i.e., ~30 dB at 4.5 vol % or ~100 dB at ~10% of functionalized nanotubes) compared with literature. The superior performance of our particular composites could be due to the uniformity of dispersion obtained through specific functionalization along with a larger aspect ratio.

Figure 9:
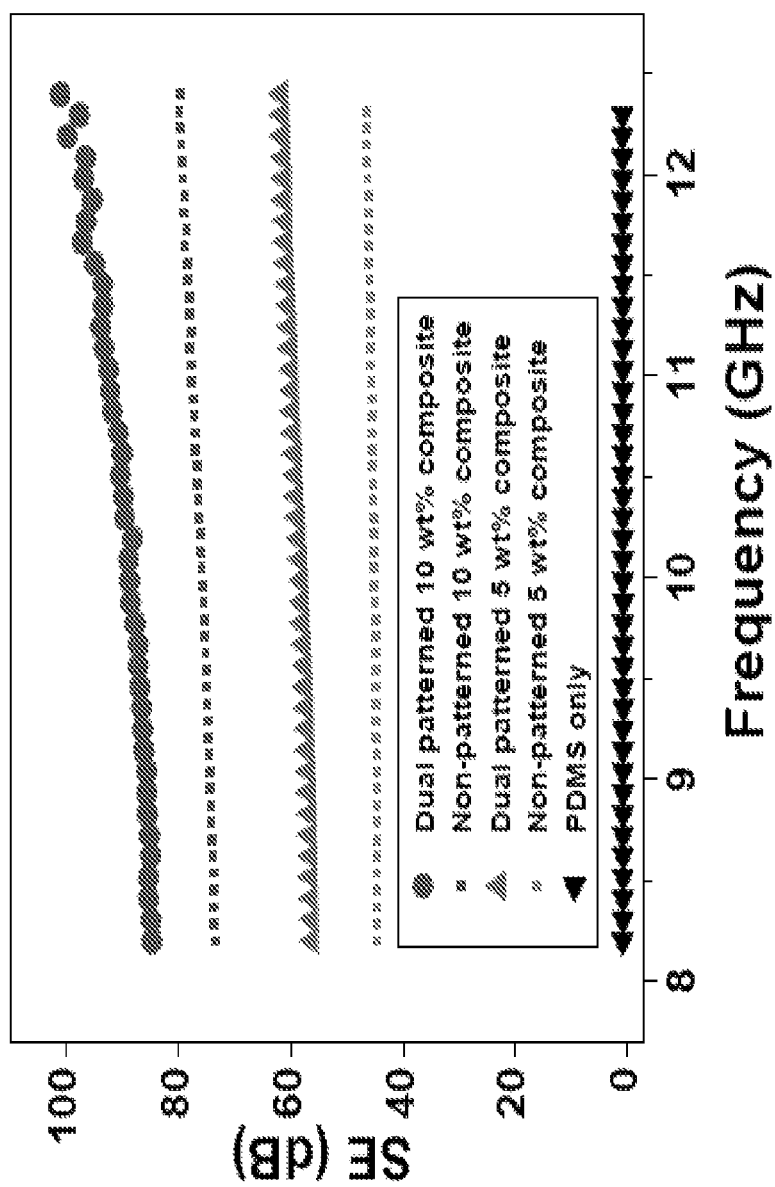
FIG. 9 depicts the variation of the shielding efficiency (SE) in the X-band (8.2 GHz-12.4 GHz) indicating that up to 100 dB of electromagnetic shielding may be obtained through the use of nanotubes as fillers of polymer matrices.

FIG. 9 depicts the variation of the shielding efficiency (SE) in the X-band (8.2 GHz-12.4 GHz) indicating that up to 100 dB of electromagnetic shielding may be obtained through the use of nanotubes as fillers of polymer matrices. The EMI shielding effectiveness (SE) of the synthesized composite may be monitored from DC to the microwave frequency range (8.2-12.4 GHz: X-band) using a two-port vector network analyzer. The X-band is used for both civil and military communications with applications as diverse as weather monitoring, vehicular detection and air traffic control and defense tracking. The desired amount of conducting filler is dependent on the required shielding effectiveness/efficiency (SE), where $$SE = 10\log\frac{P_i}{P_t}\log\frac{P_i}{P_t},$$

where $P_i$ and $P_t$ are the magnitudes of the incident and transmitted power densities and are measured through the network analyzer. The initial calibration may be performed using the TRL (Thru-Reflect-Line) method, which is an improvement over the traditional OSL (Open-Short-Load) calibration technique. In the TRL calibration, the "Thru" measurement may be first performed by connecting the two 15 cm waveguide sections directly and measures the total loss and phase delay of the setup, in the absence of the sample. For the "Reflect" calibration, an aluminum short/load may be placed between the waveguide sections, while the "Line" calibration may be done through the insertion of a quarter-wave section of waveguide (WR-90). These latter measurements serve to accurately delineate the plane of the DUT (device under test) through a consideration of the reflections and other losses prevalent in the test setup including the cabling, waveguide segments and transitions, without the sample. The scattering parameters obtained from the calibration may then be used for the baseline and the reported SE values.

Figure 10:
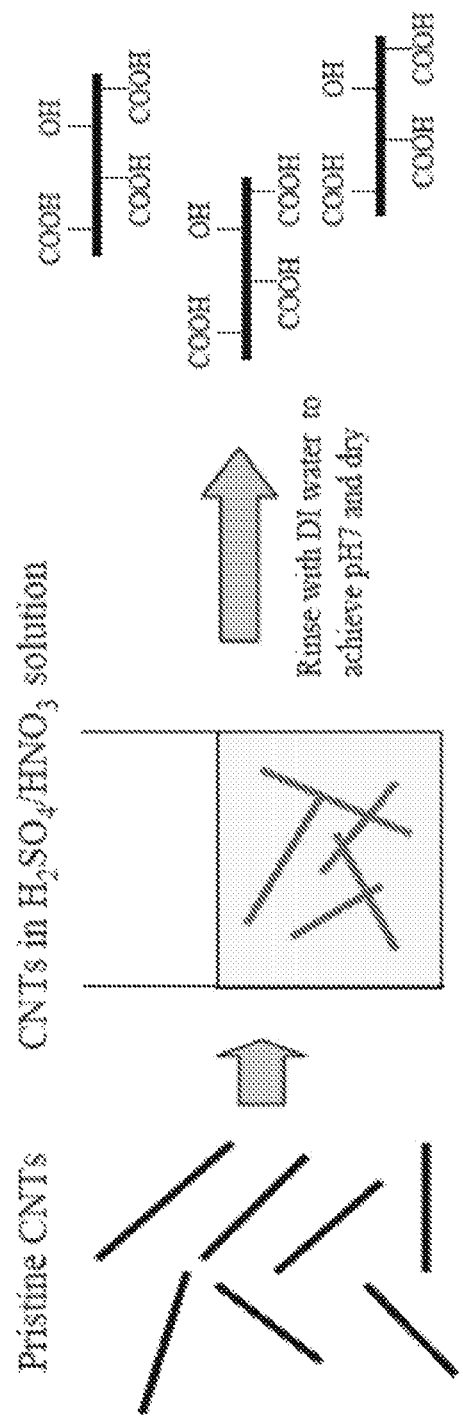
FIG. 10 is a schematic diagram of oxidation process using sulfuric and nitric acids of the used carbon nanotubes (CNTs) which yields functionalized CNT surfaces and aids the uniform dispersion of the nanostructures within the polymer matrices. Additionally, plasma processing may be used to create charged surfaces which further aids dispersion as well as increasing the electromagnetic interference and aids in the thermal robustness.

FIG. 10 is a schematic diagram of oxidation process using sulfuric and nitric acids of the used carbon nanotubes (CNTs) which yields functionalized CNT surfaces and aids the uniform dispersion of the nanostructures within the polymer matrices. Additionally, plasma processing may be used to create charged surfaces which further aids dispersion as well as increasing the electromagnetic interference and aids in the thermal robustness. To achieve homogeneous dispersion of CNTs in solvent/polymer matrix, it is often necessary to use chemical functionalization of CNTs to enable reactions with functional groups of the polymer matrix, through a condensation reaction (or esterification). For this purpose, covalent functionalization may be used to cause disruption of π-conjugation on the CNT. In some embodiments of the disclosed technology, hydroxyl (—OH), carboxyl groups (—COOH), acyl chloride or amide groups, can be formed at the defects on the CNT surface, through oxidation or acid treatment of the CNTs as schematically shown in FIG. 10, where sulfuric and nitric acids have been used for functionalization. Additionally, plasma processing may be used to create defects for nanotube/nanowire/nanocone adhesion as well as charged surfaces to further aid dispersion as well as increasing the electromagnetic interference and aids in the thermal robustness.

Figure 11:
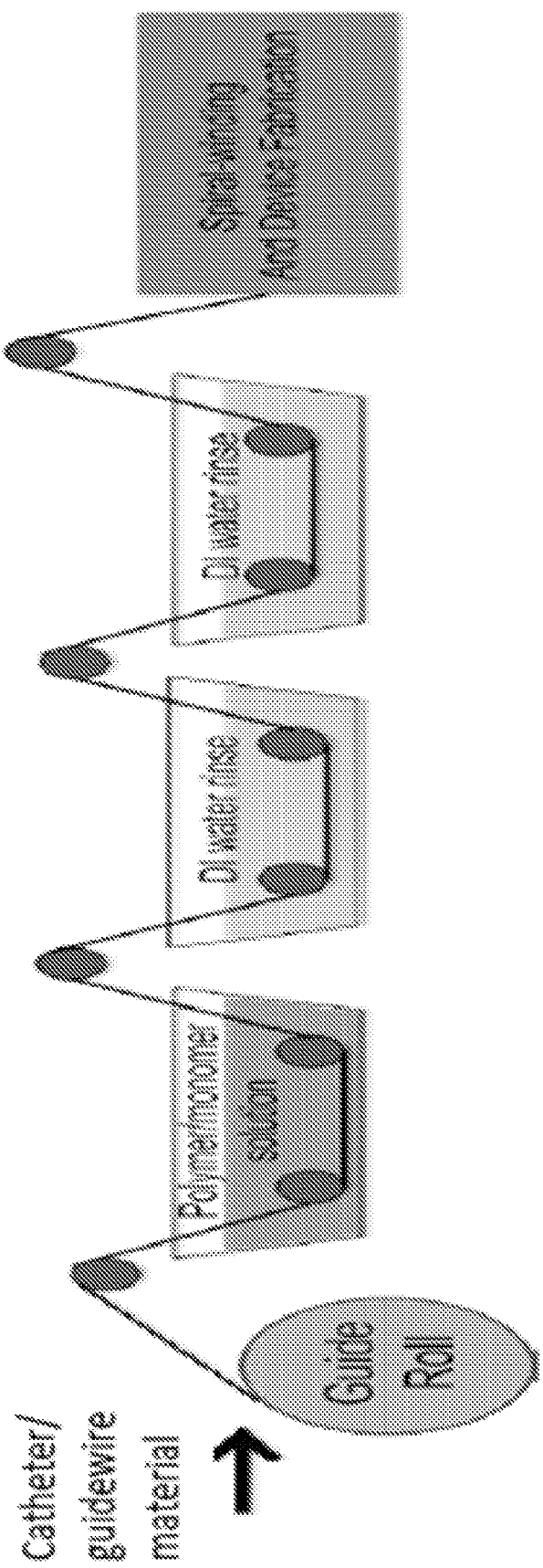
FIG. 11 is a schematic of one specific embodiment of the coating process, involving the coating of the MRI compatible catheter/guidewire through a solution (incorporating the nanostructure-polymer mixture) bath process.

FIG. 11 is a schematic of an embodiment of the coating process, involving the coating of the MRI compatible catheter/guidewire through a solution (incorporating the nanostructure-polymer mixture) bath process. The composite may be fabricated on a large scale for coating wires through a wire-drawing process, where the wire is passed through a solution (incorporating the nanostructure-polymer mixture) bath.

Figure 12:
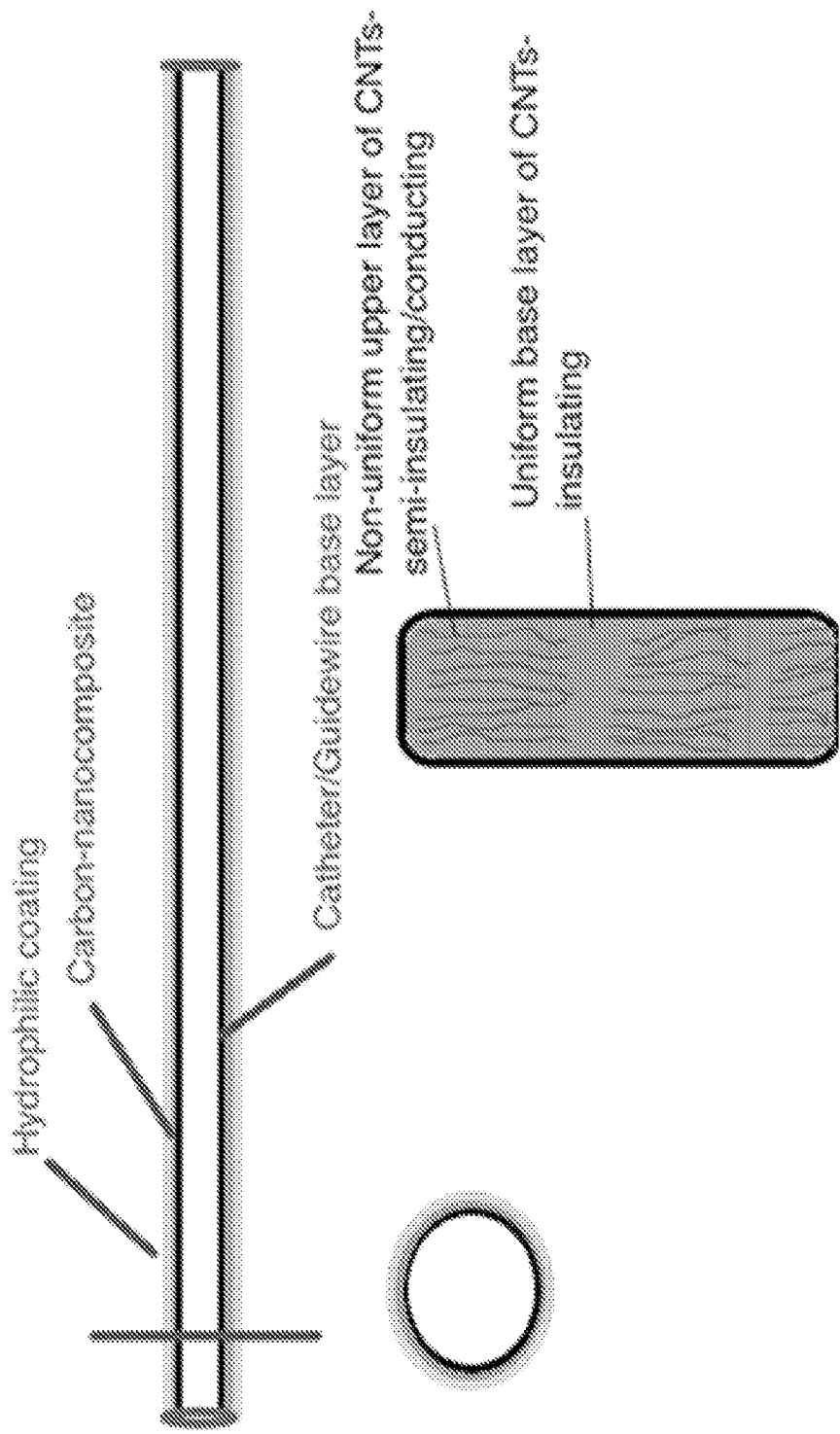
FIG. 12 is a schematic of one specific embodiment of nanocomposite coating on to the guidewire, that could be used for guidewires/catheters in minimally invasive surgery.

FIG. 12 is a schematic of one specific embodiment of nanocomposite coating on to the guidewire, that could be used for guidewires/catheters in minimally invasive surgery. The synthesis process related to FIG. 11 may be used for coating guidewires for minimally invasive surgery, for example, in magnetic resonance imaging (MRI).

In an embodiment of the disclosed technology, a guidewire device may include one or more coatings of a nanomaterial over a wire, providing the wire with altered electromagnetic and/or thermal properties. The nanomaterial may include nanotubes and/or nanowires and/or nanofibers. The nanomaterial may be electrically conductive, or may be electrically insulating. The nanomaterial may be electrically conductive, or may be electrically insulating. The guidewire device is suitable for non-invasive surgery and invasive surgery. The guidewire device may be catheter. The guidewire device may also be an access needle, a transseptal needle, an aspiration needle, an injection needle, a biopsy needle, or chemoablation needle. The guidewire device may also be a sheath and dilator. The guidewire device may also be an electrophysiology mapping, ablation, pacing, and defibrillating catheter. The guidewire device may also be a valve. The guidewire device may also be a device delivery system. The guidewire device may also be a stent and endograft. The guidewire device may also be a trocar, an access port, or an insufflator. The guidewire device may also be a laser. The guidewire device may also be a shunt. The guidewire device may also be a graft. The guidewire device may also be a snare catheter. The guidewire device may also be a balloon catheter. The guidewire device may also be an implantable device. The guidewire device incorporating the carbon nanotube/nanowire/nanofiber-polymer matrix comprised composite may be embedded with non-active fiducial markers. The guidewire device incorporating the carbon nanotube/nanowire/nanofiber-polymer matrix comprised composite may be embedded with active electronic elements.

In another embodiment of the disclosed technology, a method of manufacturing the guidewire device discussed above may include using carbon nanotube and/or nanowire and/or nanofiber of differing mean length to mean diameter aspect ratios, wherein the varying aspect ratio provide capability to tune electrical conductivity and thermal conductivity of the guidewire. In another embodiment of the disclosed technology, a method of manufacturing the guidewire device discussed above may include coating the carbon nanotube/nanowire/nanofiber-polymer matrix comprised composite. In another embodiment of the disclosed technology, a method of manufacturing the guidewire device discussed above may include spray coating a composite comprising a carbon nanotube/nanowire/nanofiber-polymer matrix over a metallic wire. In another embodiment of the disclosed technology, a method of manufacturing the guidewire device discussed above may include fabricating the guidewire device using a carbon nanomaterial including inner and outer non-conductive coatings and a middle layer of conductive coating. In another embodiment of the disclosed technology, a method of manufacturing the guidewire device discussed above may include placing spacers along a length of the guidewire device, wherein the spacers are made of carbon-based nanomaterial.

Some embodiments of the disclosed technology can be implemented using various coatings, for example, including coatings of carbon nanotube/nanowire/nanofiber-polymer matrix comprised composite, for electromagnetic interference (EMI) shielding compatibility, coatings of carbon nanotube/nanowire/nanofiber-polymer matrix comprised composite, for reduced thermal parasitic effects, coatings of carbon nanotube/nanowire/nanofiber-polymer matrix comprised composite, for enhanced imaging modalities, for example, in magnetic resonance imaging, coatings of carbon nanotube/nanowire/nanofiber-polymer matrix comprised composite, for medical equipment, and coatings of carbon nanotube/nanowire/nanofiber-polymer matrix comprised composite, for surface coverage in medical equipment containing rooms.

Some embodiments of the disclosed technology can be used to operate a nanocomposite-based guidewire device in a minimally invasive surgery procedure. The guidewire device comprises a combination of non-active and/or active marker. The surgery procedure includes one of a cardiovascular surgery, peripheral vascular surgery, urological surgery, oncological surgery, and neurovascular surgery. The composite constituted markers are periodically placed on the guidewire device. The resonance or scattering conditions are imposed along a length of the device through surface patterning. The electrical and thermal conductivity of a tip of the guidewire device is actively or passively modulated or modified through composite coatings constituted from various nanomaterials. Some embodiments of the disclosed technology can be applied to use composite coating methodologies and wires for external and in vitro use as wires in electrophysiology, including electrocardiography.

In another embodiment of the disclosed technology, a guidewire device includes a guidewire base layer for placement of a medical equipment, and one or more coatings including a polymer matrix and a nanomaterial over the guidewire base layer providing the guidewire device with electromagnetic compatibility and reduced thermal parasitics. For example, the nanomaterial includes oblong shape filler composite materials dispersed in the polymer matrix. Here, the nanomaterial may include nanotubes or nanowires or nanofibers or combination of any two or more of nanotubes, nanowires, and nanofibers with or without others. The nanomaterial may include single-walled carbon nanotubes or multiwalled carbon nanotubes dispersed into the polymer matrix. The single-walled carbon nanotubes or multiwalled carbon nanotubes may include carboxyl group functionalized single-walled carbon nanotubes or multiwalled carbon nanotubes. The polymer matrix may include a reactive ethylene terpolymer (RET) including an epoxide functional group. The guidewire base layer for placement of the medical equipment with the one or more coatings including the polymer matrix and the nanomaterial has imaging modalities in magnetic resonance imaging and electromagnetic interference (EMI) shielding compatibility. The one or more coatings including the polymer matrix and the nanomaterial may be embedded with active electronic elements. The one or more coatings including the polymer matrix and the nanomaterial may be embedded with non-active fiducial markers. The nanomaterial may include a carbon nanomaterial including inner and outer non-conductive coatings and a middle layer of conductive coating. The guidewire device may further include spacers along a length of the guidewire device, wherein the spacers are made of carbon based nanomaterial. The one or more coatings including the polymer matrix and the nanomaterial include uniform base layers of carbon nanotubes as the polymer matrix and non-uniform upper layers of carbon nanotubes as the nanomaterial.

In another embodiment of the disclosed technology, a method of manufacturing a guidewire device may include preparing a guidewire base layer for placement of a medical equipment, preparing coating solution by incorporating a nanostructure-polymer mixture including oblong shape filler composite materials of differing mean length to mean diameter aspect ratios, wherein the varying aspect ratio provide capability to tune electrical conductivity and thermal conductivity of the guidewire device, and applying the coating solution on a surface of the guidewire base layer to form a coating on the guidewire base layer.

Various embodiments of the disclosed technology can take a variety of forms other than those described in detail in this application. For example, carbon nanotubes are only one form of nanotubes that potentially could be employed. While operation of the nanotubes in a polymeric matrix, for guidewires and catheters is described above, other operational circumstances are also possible. Also, as mentioned above, various forms can be employed in a variety of different types of electromagnetic interference shielding devices, not merely guidewires or catheter based devices. Also, while the above-described device may operate in a large range of frequency, from DC (0 Hz) to ultra-high frequency (Terahertz). When integrated with active device (e.g., transistor) technology, devices such as those described above offer a possible solution to the problem of guidewire scaling coupled with the advantages of high density integrated circuitry and a faster speed of operation.

Although exemplary methods of operating and fabricating guidewire devices in accordance with at least some embodiments have been described above, the techniques are further intended to encompass other methods of operating and fabricating related devices as well. For example, embodiments may encompass any operational methods and instrumentation that involve using the EMI compatible, thermally robust and enhanced imaging modalities. For example, the coating technology could be used for enhancing the EMI immunity of equipment and ambient (walls) of the surroundings of the MRI equipment. Also for example, embodiments may encompass any methods of manufacturing guidewire or EMI compatible, thermally robust devices that involve the formation of carbon nanotubes nanowires/nanocones/nanofibers within polymer matrices for coating technologies in medicine related environments.

It is specifically intended that embodiments not be limited to the embodiments and illustrations contained herein, but include modified forms of those embodiments including portions of the embodiments and combinations of elements of different embodiments as come within the scope of the following claims.

We claim:
1. A device comprising:
a base layer that is part of a medical instrument; and
one or more coatings of a nanomaterial structure over the base layer, the nanomaterial structure including a polymer matrix and a plurality of nanomaterial fillers dispersed in the polymer matrix such that the plurality of nanomaterial fillers are aligned in a plane of the polymer matrix,
wherein the polymer matrix includes reactive ethylene terpolymer (RET) matrix including an epoxide functional group and nanomaterial fillers includes carboxyl group functionalized single-walled carbon nanotubes or multiwalled carbon nanotubes to form ester bond linkages between the carboxyl group functionalized nanotubes and the epoxide functional group.

2. The device of claim 1, wherein the plurality of nanomaterial fillers comprises at least one of nanotubes, nanowires, or nanofibers.

3. The device of claim 1, wherein the medical instrument includes a device suitable for non-invasive surgery.

4. The device of claims 1, wherein base layer is at least a portion of a catheter, an access needle, a transseptal needle, an aspiration needle, an injection needle, a biopsy needle, a chemoablation needle, a medical sheath, a medical dilator, a valve, a device delivery system, a stent, an endograft, a trocar, an access port, an insufflator, a laser device, a shunt, a graft, a snare catheter, a balloon catheter, or an implantable device.

5. The device of claim 1, wherein the plurality of nanomaterial fillers includes oblong shape filler composite materials.

6. The device of claim 1, wherein the plurality of nanomaterial fillers includes nanomaterial fillers with various length to mean diameter aspect ratios to tune electrical conductivity and thermal conductivity of the nanomaterial structure.

7. The device of claim 1, wherein the plurality of nanomaterial fillers comprises a carbon-based nanomaterial.

8. The device of claim 7, wherein the carbon-based nanomaterial includes carbon black spheres.

9. The device of claim 1, wherein the plurality of nanomaterial fillers is arranged in the polymer matrix to change an electrical conductivity of the nanomaterial structure.

10. The device of claim 1, wherein the plurality of nanomaterial fillers is arranged in the polymer matrix to change a thermal conductivity of the nanomaterial structure.

11. The device of claim 1, wherein the device is embedded with non-active fiducial markers.

12. The device of claim 1, wherein the device is embedded with active electronic elements.

13. The device of claim 1, further comprising at least one of a non-active marker or an active marker.

14. The device of claim 1, further comprising a plurality of markers periodically placed on the device.

15. A method of manufacturing a medical device, comprising:
synthesizing a composite that includes a polymer matrix and a plurality of nanomaterial fillers dispersed in the polymer matrix; and
forming a layer of the composite along a surface of a base layer of the medical device such that the plurality of nanomaterial fillers are aligned in a plane of the polymer matrix,
wherein the polymer matrix includes reactive ethylene terpolymer (RET) matrix including an epoxide functional group and nanomaterial fillers includes carboxyl group functionalized single-walled carbon nanotubes or multiwalled carbon nanotubes to form ester bond linkages between the carboxyl group functionalized nanotubes and the epoxide functional group.

16. The method of claim 15, wherein the forming the layer of the composite includes spray coating the composite along the surface of the base layer.

* * * * *